(12) United States Patent
Mizusawa

(10) Patent No.: US 8,730,592 B2
(45) Date of Patent: May 20, 2014

(54) OPTICAL SYSTEM

(75) Inventor: Masayuki Mizusawa, Hachioji (JP)

(73) Assignee: Olympus Corporation, Tokyo (JP)

( * ) Notice: Subject to any disclaimer, the term of this patent is extended or adjusted under 35 U.S.C. 154(b) by 131 days.

(21) Appl. No.: 13/138,222

(22) PCT Filed: Jan. 21, 2010

(86) PCT No.: PCT/JP2010/050714
§ 371 (c)(1),
(2), (4) Date: Jul. 19, 2011

(87) PCT Pub. No.: WO2010/084915
PCT Pub. Date: Jul. 29, 2010

(65) Prior Publication Data
US 2011/0273784 A1    Nov. 10, 2011

(30) Foreign Application Priority Data

Jan. 21, 2009  (JP) .................................. 2009-010695
Mar. 19, 2009  (JP) .................................. 2009-068400

(51) Int. Cl.
*G02B 17/08* (2006.01)
(52) U.S. Cl.
CPC ................................ G02B 17/0856 (2013.01)
USPC ......................................... 359/727; 359/784
(58) Field of Classification Search
CPC ...................................... G02B 17/08–17/0896
USPC ......... 359/726–732, 754–756, 761, 763, 770, 359/771, 781–784
See application file for complete search history.

(56) References Cited

U.S. PATENT DOCUMENTS 7,929,219 B2 *  4/2011  Togino .......................... 359/736
2010/0110564 A1 *  5/2010  Togino .......................... 359/725

FOREIGN PATENT DOCUMENTS

| JP | 07-318799 | 12/1995 |
| JP | 2001-267594 | 9/2001 |
| WO | 03/042743 | 5/2003 |
| WO | 2005/110186 | 11/2005 |
| WO | WO 2008/153114 | 12/2008 |

* cited by examiner

*Primary Examiner* — Darryl J Collins
(74) *Attorney, Agent, or Firm* — Kenyon & Kenyon LLP

(57) ABSTRACT

An optical system for viewing a front object and a generally side object comprises, sequentially from the front object side, a first lens group having a negative refractive index, a second lens group including a reflective-refractive lens, an aperture stop, and a third lens group having a positive refractive index. The reflective-refractive lens is provided with a first surface formed on the front object side, a second surface formed on an image side, and a third surface formed circumferentially to surround an optical axis between the first surface and the second surface. The first surface is provided with a first transmission surface formed around the optical axis, and a first reflection surface that faces the image side and is formed around the first transmission surface. The first surface is defined by an aspherical surface consisting of a concave surface in the vicinity of the optical axis and a convex surface in the vicinity of the first reflection surface. The second surface is provided with a second transmission surface formed around the optical axis and a second reflection surface that faces the front object side and that is formed around the second transmission surface. The third surface is defined by a transmission surface.

6 Claims, 19 Drawing Sheets

(a)

(b)

(a)    (b)

(a)

(b)

OPTICAL SYSTEM

TECHNICAL FIELD

This invention relates to an optical system by which a front object and an approximately lateral object can be simultaneously observed.

BACKGROUND ART

Optical systems by which a front object and an approximately lateral object can be simultaneously observed have been known, up to now. In this case, the range which the above term, "approximately lateral", defines includes not only the lateral side of an optical system itself but also the diagonally forward and diagonally backward sides of the optical system.

In such optical systems, an optical system which is formed in such a way that, after light from the approximately-lateral-object side is reflected two times on the inside, the light emerges to the image side has been known (for example, refer to International Publication No. 2003/042743).

DISCLOSURE OF INVENTION

However, in the optical system which is described in International Publication No. 2003/042743, after light from the approximately-lateral-object side is reflected by two members, the light emerges to the image side. Accordingly, the optical system which is described in International Publication No. 2003/042743 has a problem that, in the case where cumulative tolerance between these members and a lens barrel or the like that holds these members becomes large, one of these members easily becomes eccentric to the other of these members in assembling the optical unit, and the capability of forming an image easily deteriorates.

The present invention is made in view of such a conventional technical problem. The object of the present invention is to offer an optical system which can restrain the deterioration of the capability of forming an image.

In order to achieve the above-described object, an optical system of the present invention for observing a front object and an approximately lateral object is characterized in that: a first lens group with negative refractive power, a second lens group including a reflective-refractive lens, an aperture stop, and a third lens group with positive refractive power are arranged in that order from the front-object side; the reflective-refractive lens is provided with a first surface which is formed on the front-object side, a second surface which is formed on the image side, and a third surface which is formed between the first and second surfaces in the circumferential direction so that the optical axis is surrounded by the third surface; the first surface includes a first transmission surface which is formed with the center of the first transmission surface being on the optical axis and a first reflection surface which faces toward the image side and is formed around the first transmission surface, and the first surface is an aspherical surface which has a concave-surface shape in the vicinity of the optical axis and a convex-surface shape in the vicinity of the first reflection surface; the second surface includes a second transmission surface which is formed with the center of the second transmission surface being on the optical axis and a second reflection surface which faces toward the front-object side and is formed around the second transmission surface; and the third surface is a transmission surface.

Also, in an optical system of the present invention, it is preferred that: after light from the front-object side is incident on the first transmission surface, the light emerges from the second transmission surface to the image side; and after light from the approximately-lateral-object side is incident on the third surface, the light is reflected by the second reflection surface and the first reflection surface in that order and emerges from the second transmission surface to the image side.

Also, in an optical system of the present invention, it is preferred that the following condition is satisfied:

$$2 < R_{21\_1}/f_{F\_21} < 30$$

where $f_{F\_21}$ denotes the focal length of the reflective-refractive lens relative to paraxial light rays in light from the front-object side, and $R_{21\_1}$ denotes the paraxial radius of curvature of the first surface of the reflective-refractive lens.

Also, in an optical system of the present invention, it is preferred that the following condition is satisfied:

$$1/f_{s\_21\_Mid} < 1/f_{s\_21\_Max}$$

where $f_{s\_21\_Mid}$ denotes the focal length of the reflective-refractive lens relative to light the chief ray of which passes through the middle angle of view in light from the approximately-lateral-object side, and $f_{s\_21\_Max}$ denotes the focal length of the reflective-refractive lens relative to light the chief ray of which passes through the maximum angle of view in light from the approximately-lateral-object side.

Also, in an optical system of the present invention, it is preferred that the following condition is satisfied:

$$f_{s\_21\_Mid} < 0$$

where $f_{s\_21\_Mid}$ denotes the focal length of the reflective-refractive lens relative to light the chief ray of which passes through the middle angle of view in light from the approximately-lateral-object side.

Also, in an optical system of the present invention, it is preferred that the following condition is satisfied:

$$f_{s\_Mid} < f_{s\_Max}$$

where $f_{s\_Mid}$ denotes the focal length of the optical system relative to light the chief ray of which passes through the middle angle of view in light from the approximately-lateral-object side, and $f_{s\_Max}$ denotes the focal length of the optical system relative to light the chief ray of which passes through the maximum angle of view in light from the approximately-lateral-object side.

According to the present invention, it is possible to offer an optical system which can restrain the deterioration of the capability of forming an image.

BEST CONFIGURATION FOR EMBODYING INVENTION

Figure 1:
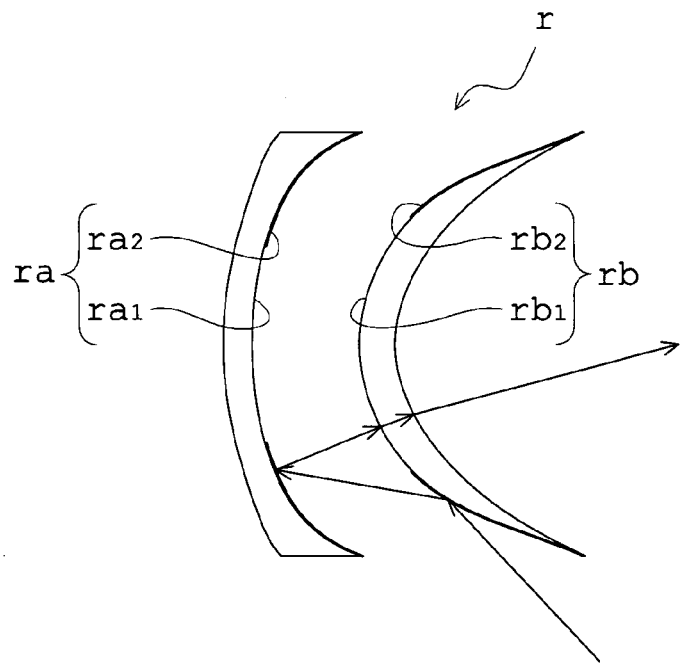
FIG. 1 is a schematic view showing the optical path of light from the approximately-lateral-object side, (a) shows an optical path in a conventional reflective-refractive member for optical system and in the vicinity of the reflective-refractive member, and (b) shows an optical path in a reflective-refractive member (reflective-refractive lens) for optical system of the present embodiments and in the vicinity of the reflective-refractive member.
Figure 1:
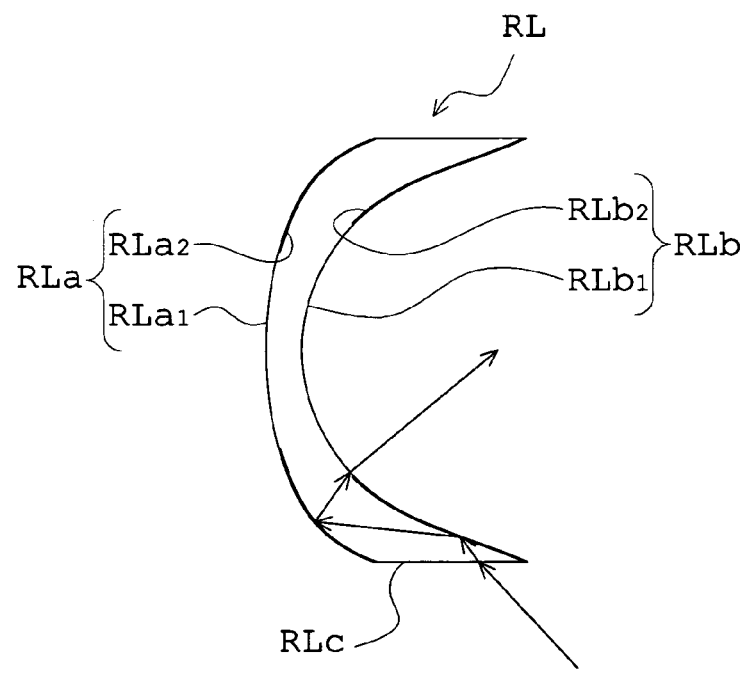

Prior to the explanations of the embodiments for optical systems of the present invention, operation effects which are caused by the constitutions according to the present embodiments will be explained using the drawings.

In the optical systems of the present embodiments, a first lens group with negative refractive power, a second lens group including a reflective-refractive lens, an aperture stop, and a third lens group with positive refractive power are arranged in that order from the front-object side.

And, the reflective-refractive lens which is included by the second lens group includes a first surface which is formed on the front-object side, a second surface which is formed on the image side, and a third surface which is formed between the first and second surfaces in the circumferential direction so that the optical axis is surrounded by the third surface.

In this case, the first surface includes a first transmission surface which is formed with the center of the first transmission surface being on the optical axis and a first reflection surface which faces toward the image side and is formed around the first transmission surface and in the shape of a ring. Also, the first surface has an aspherical surface shape by which the first surface becomes a concave surface in the vicinity of the optical axis and convex surface in the vicinity of the first reflection surface. As a result, the first surface has a function as negative lens on light rays that are transmitted in the vicinity of the center and a function as positive lens on light rays that are reflected by the first reflection surface. The second surface includes a second transmission surface which is formed with the center of the second transmission surface being on the optical axis and a second reflection surface which faces toward the front-object side and is formed around the second transmission surface and in the shape of a ring. The third surface is a transmission surface. This third surface may be formed on part of the peripheral surface between the first and second surfaces or on the whole of the peripheral surface between the first and second surfaces.

Besides, after entering the first transmission surface, light which enter the reflective-refractive lens from the front-object side emerges from the second transmission surface to the image side. Also, after entering the third surface, light which enters the reflective-refractive lens from the approximately-lateral-object side is reflected by the second reflection surface and the first reflection surface in that order and emerges from the second transmission surface to the image side.

As described above, in the optical systems of the present embodiments which are different from conventional optical systems, members which reflect and refract light from the approximately-lateral-object side are composed of one member. That is to say, in the members for the present embodiments which reflect and refract light, air does not fill the spaces between the reflection surfaces of each of the members, but glass or the like fills the spaces between the reflection surfaces.

Now, the difference between reflective-refractive members for optical systems of the present embodiments and reflective-refractive members for conventional optical systems that reflect and refract light from the approximately-lateral-object side is explained using FIG. 1. This FIG. 1 is a schematic view showing an optical path of light from the approximately-lateral-object side, (a) shows an optical path in a conventional reflective-refractive member for optical system and in the vicinity of the reflective-refractive member, and (b) shows an optical path in a reflective-refractive member for optical systems of present embodiments and in the vicinity of the reflective-refractive member. In this case, "reflective-refractive member" means a member which uses reflection function and refraction function of light.

As shown in FIG. 1(a), a conventional reflective-refractive member r for optical system consists of a first reflection member ra and a second reflection member rb. Besides, the first reflection member ra includes: a transmission surface $ra_1$ which is formed with the center of the transmission surface being on the optical axis; and a reflection surface $ra_2$ which is formed around the transmission surface and in the shape of a ring and faces toward the image side. Also, the second reflection member rb includes: a transmission surface $rb_1$ which is formed with the center of the transmission surface being on the optical axis; and a reflection surface $rb_2$ which is formed around the transmission surface and in the shape of a ring and faces toward the front-object side. Accordingly, the first reflection member ra and the second reflection member rb include only one reflection surface respectively, so that the two reflection surfaces of the reflective-refractive member r are formed by members which are different from each other, respectively.

On the other hand, as shown in FIG. 1(b), a reflective-refractive member for optical systems of the present embodiments is composed of only a reflective-refractive lens RL. That is to say, in the present embodiments, two reflection surfaces of the reflective-refractive lens RL are formed by one member. Besides, the reflective-refractive lens RL includes: a first surface RLa which is formed on the front-object side and through which light from the front-object side enters; a second surface RLb which is formed on the image side; and a third surface RLc which is formed between the first and second surfaces and in the circumferential direction so that the optical axis is surrounded by the third surface and through which light from the approximately-lateral-object side enters. The first surface RLa of the lens RL includes: a first transmission surface $RLa_1$ which is formed with the center of the first transmission surface being on the optical axis; and a first reflection surface $RLa_2$ which faces toward the image side and is formed around the first transmission surface $RLa_1$ and in the shape of a ring. The second surface RLb includes: a second transmission surface $RLb_1$ which is formed with the center of the second transmission surface being on the optical axis; and a second reflection surface $RLb_2$ which faces toward the front-object side and is formed around the second transmission surface $RLb_1$ and in the shape of a ring.

Besides, this reflective-refractive lens RL for optical systems of the present embodiments may be a cemented lens. Also, the first reflection surface $RLa_2$ and the second reflection surface $RLb_2$ of this reflective-refractive lens RL are formed through vapor deposition. Specifically, for example, after a mask which has the same shape as that of the first transmission surface $RLa_1$ is put on the first transmission surface $RLa_1$, the whole of the first surface RLa is given mirror coating, and then, the mask is peeled off from the first transmission surface $RLa_1$. A masked part of the first surface RLa is not given mirror coating by the use of such a method, so that the first transmission surface $RLa_1$ can be used as a transmission surface even after the first reflection surface $RLa_2$ is formed. Besides, methods for forming the first reflection surface $RLa_2$ and the second reflection surface $RLb_2$ are not limited to the above-described manner. Also, the third surface RLc of this reflective-refractive lens RL may be formed in such a way that the front-object-side diameter of the third surface is as large as the image-side diameter of the third surface, or in such a way that the image-side diameter of the third surface is smaller or larger than the front-object-side diameter of the third surface.

As shown in this FIG. 1, a reflective-refractive member for optical systems of the present embodiments is composed of a reflective-refractive lens RL that is a single member. That is to say, in the reflective-refractive lens RL, the space between the two reflection surfaces is filled with medium which is different from air. Accordingly, the reflective-refractive lens RL can refract light from the approximately-lateral-object side, on the third surface RLc which is formed between the two reflection surfaces and in the circumferential direction. As a result, the interval between the two reflection surfaces can be made to become smaller, as compared with the case where the space between two reflection surfaces is filled with air. Specifically, for example, on the one hand, in the case of the optical system which is one of conventional examples and is disclosed as the embodiment 1 in International Publication No. 2003/042743, the distance between the two reflection surfaces on the optical axis amounts up to about 4.9 times as long as the focal length relative to light from the front-object side, but on the other hand, in the cases of the optical systems of the present embodiments, the distance between the two reflection surfaces on the optical axis can be held up to about 1.4 times as long as the focal length relative to light from the front-object side.

As described above, even in the case where the reflective-refractive lens RL is formed in such a way that the reflective-refractive lens RL for optical systems of the present embodiments has the same angle of view as that of a conventional reflective-refractive member r for optical system, it is possible to greatly thin the thickness of the reflective-refractive lens RL in the direction along the optical axis of light from the front-object side.

It is preferred that the optical systems of the present embodiments are formed in such a way that the following condition (1) is satisfied:

$$2 < R_{21\_1}/f_{F\_21} < 30 \qquad (1)$$

where $f_{F\_21}$ denotes the focal length of the reflective-refractive lens relative to paraxial light rays in light from the front-object side, and $R_{21\_1}$ denotes the paraxial radius of curvature of the first surface of the reflective-refractive lens.

This condition (1) prescribes the paraxial radius of curvature of the first surface which is formed in the shape of an aspherical surface that has a concave-surface shape in the vicinity of the center and a convex-surface shape in the vicinity of the first reflection surface, in the surfaces that the reflective-refractive lens includes. If $R_{21\_1}/f_{F\_21}$ is below the lower limit in the condition (1), the paraxial radius of curvature of the first surface becomes too small relative to the focal length of the reflective-refractive lens. That is to say, the paraxial curvature of the first surface becomes too large. In this case, the refractive power of the first surface sharply changes from negative refractive power to positive refractive power in the range from the paraxial position to the first reflection surface. That is to say, because the slope at an inflection point at which the first surface changes from a concave surface to a convex surface becomes too large, it is difficult to work the reflective-refractive lens into an aspherical shape. On the other hand, if $R_{21\_1}/f_{F\_21}$ is beyond the upper limit in the condition (1), the paraxial radius of curvature of the first surface becomes too large. That is to say, the paraxial curvature of the first surface becomes too small. In this case, because the refractive power of the first surface becomes small, the necessity of making the negative refractive power of the second surface and the negative refractive power of the first lens group larger occurs. As a result, spherical aberration inevitably becomes worse.

Figure 2:
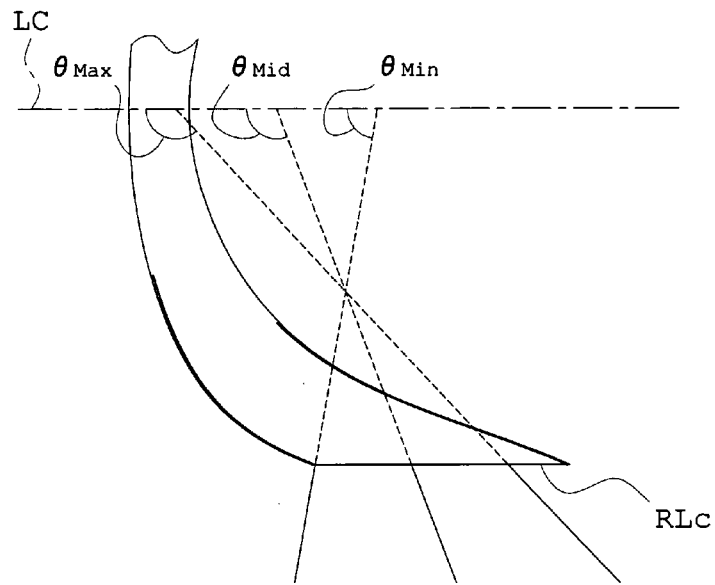
FIG. 2 is a schematic view showing angles of view in reflective-refractive lenses which optical systems of the present embodiments include, relative to light which enters the reflective-refractive members from the approximately-lateral-object side.

Now, the definition of angle of view of light that enters a reflective-refractive lens for optical systems of the present embodiments from the approximately-lateral-object side is explained using the schematic view of FIG. 2.

The chief ray of light entering from the approximately-lateral-object side enters through the third surface RLc of the reflective-refractive lens RL, and the angle which is formed between the chief ray and the optical axis LC on the front-object side becomes a half angle of view on the approximately-lateral-object side of the reflective-refractive lens RL.

Also, in the case of such a reflective-refractive lens RL, it is impossible to observe a front object, or an object existing on the optical axis LC, through the third surface RLc. Accordingly, the angles of view must include the minimum angle of view $\theta_{Min}$ and the maximum angle of view $\theta_{Max}$. In this case, "the minimum angle of view $\theta_{Min}$" means the angle $\theta_{Min}$ which is formed between the chief ray of the nearest light to the front-object side and the optical axis in the range in which an object can be observed through the third surface RLc. On the other hand, "the maximum angle of view $\theta_{Max}$" means the angle $\theta_{Max}$ which is formed between the chief ray of the nearest light to the to image side and the optical axis in the range in which an object can be observed through the third surface RLc. Besides, an angle which is between these angles is a middle angle of view $\theta_{Mid}$.

Figure 3:
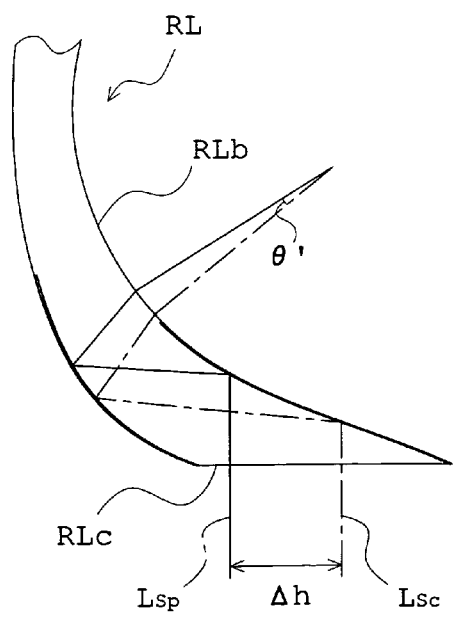
FIG. 3 is a schematic view showing the relation between the chief ray of light entering from the approximately-lateral-object side and a light ray near to the chief ray, relative to the reflective-refractive lenses which the optical systems of the present embodiments include, and (a) shows the case where the reflective-refractive lenses have a positive focal length for light from the approximately-lateral-object side and (b) shows the case where the reflective-refractive lenses have a negative focal length for light from the approximately-lateral-object side, respectively.
Figure 3:
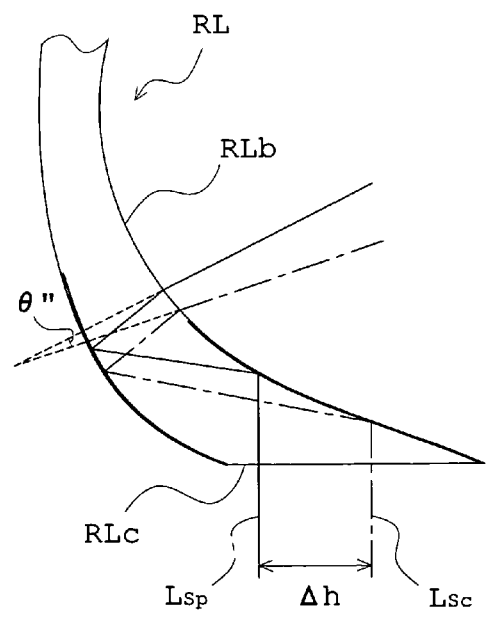

Next, the definition of the focal length of light that enters a reflective-refractive lens for optical systems of the present embodiments from the approximately-lateral-object side is explained using FIG. 3. FIG. 3 is a schematic view showing the relation between the chief ray of light entering from the approximately-lateral-object side and a light ray near to the chief ray, relative to reflective-refractive lenses for the optical systems of the present embodiments, and (a) shows the case where the reflective-refractive lenses have a positive focal length for light from the approximately-lateral-object side and (b) shows the case where the reflective-refractive lenses have a negative focal length for light from the approximately-lateral-object side, respectively.

First, it is supposed that the chief ray $L_{Sc}$ of light from the approximately-lateral-object side and a nearby light ray $L_{Sp}$ which is parallel to the chief ray $L_{Sc}$ enter the third surface RLc on the approximately-lateral side of the reflective-refractive lens RL and the distance between the chief ray $L_{Sc}$ and the nearby light ray $L_{Sp}$ is $\Delta h$ (refer to FIG. 3(a)).

In this case, if the reflective-refractive lens RL has a positive focal length, then, as shown in FIG. 3(a), after the chief ray $L_{Sc}$ and the nearby light ray $L_{Sp}$ emerge from the second surface RLb of the reflective-refractive lens RL, the chief ray $L_{Sc}$ and the nearby light ray $L_{Sp}$ focus on a predetermined point which is nearer to the image side than the second surface RLb of the reflective-refractive lens RL. And, in the case where $\theta'$ denotes the angle which is formed between these light rays when the light rays focus on the predetermined point, if $\theta'$ is in the range in which $\theta'$ satisfies $\tan \theta' = \theta'$, then the focal length $f_{S\_21}$ can be defined as the following condition:

$$f_{S\_21} = \Delta h / \theta'$$

On the other hand, if the reflective-refractive lens RL has a negative focal length, then, as shown in FIG. 3(b), after the chief ray $L_{Sc}$ and the nearby light ray $L_{Sp}$ emerge from the second surface RLb of the reflective-refractive lens RL, the chief ray $L_{Sc}$ and the nearby light ray $L_{Sp}$ diverge. In this case, when the optical path which the chief ray $L_{Sc}$ follows after the chief ray $L_{Sc}$ emerges from the second surface RLb and the optical path which the nearby light ray $L_{Sp}$ follows after the nearby light ray $L_{Sp}$ emerges from the second surface RLb are extended toward the object side, these optical paths cross each other at a predetermined point. And, in the case where $\theta''$ denotes the angle which is formed between these extended optical paths when the extended optical paths cross each other, if $\theta''$ is in the range in which $\theta''$ satisfies $\tan \theta'' = \theta''$, then the focal length $f_{S\_21}$ can be defined as the following condition:

$$f_{S\_21} = -\Delta h / \theta''$$

Also, in the optical systems of the present embodiments, it is preferred that the following condition (2) is satisfied:

$$1/f_{s\_21\_Mid} < 1/f_{s\_21\_Max} \quad (2)$$

where $f_{s\_21\_Mid}$ denotes the focal length of the reflective-refractive lens relative to light the chief ray of which passes through the middle angle of view in light from the approximately-lateral-object side, and $f_{s\_21\_Max}$ denotes the focal length of the reflective-refractive lens relative to light the chief ray of which passes through the maximum angle of view in light from the approximately-lateral-object side.

This condition (2) prescribes refractive power of the reflective-refractive lens relative to light having the maximum angle of view in light from the approximately-lateral-object side. In the case where this condition (2) is not satisfied, the refractive power of the reflective-refractive lens relative to light which enters the reflective-refractive lens at the maximum angle of view becomes larger in the negative direction than the refractive power relative to light which enters the reflective-refractive lens at the middle angle of view.

Figure 4:
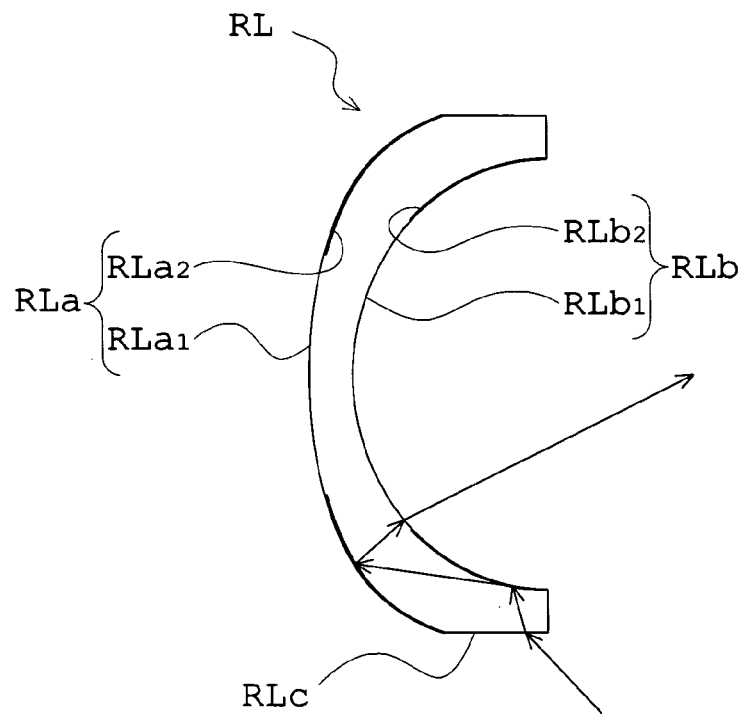
FIG. 4 is a schematic view showing the optical path of light the chief ray of which passes through the maximum angle of view in light from the approximately-lateral-object side, in the vicinities of reflective-refractive lenses for the optical systems of the present embodiments, (a) shows a reflective-refractive lens which satisfies the condition (1), and (b) shows a reflective-refractive lens which does not satisfy the condition (1).
Figure 4:
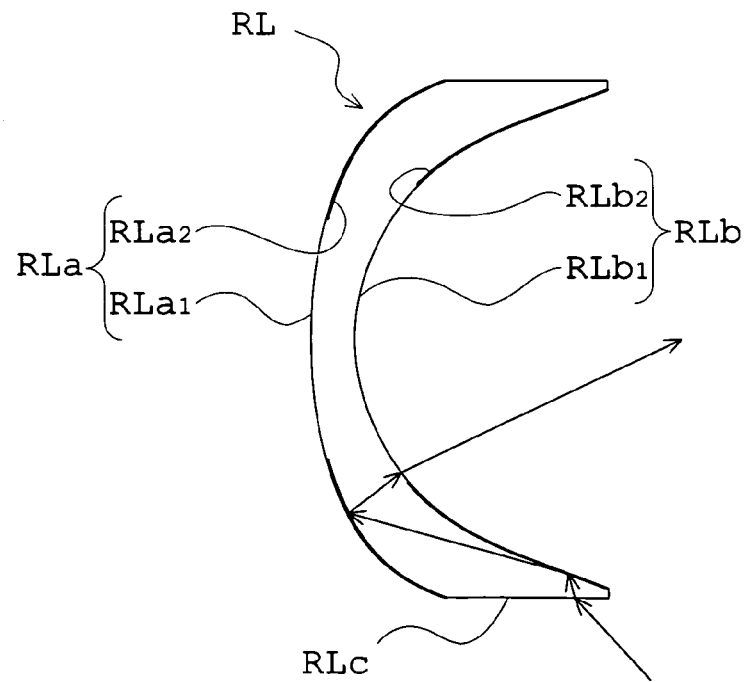

Now, an operation effect caused by satisfying the condition (2) is explained using FIG. 4. This FIG. 4 is a schematic view showing the optical path of light the chief ray of which passes through the maximum angle of view in light from the approximately-lateral-object side, in the vicinities of reflective-refractive lenses for the optical systems of the present embodiments. Besides, a reflective-refractive lens which is shown in FIG. 4(*a*) satisfies the condition (2), and a reflective-refractive lens which is shown in FIG. 4(*b*) does not satisfy the condition (2). Also, components which are shown in FIG. 4 are given the same symbols as those which are shown in FIG. 1 when the components which are shown in FIG. 4 are identical to one of the components which are shown in FIG. 1, and the explanations of these components are omitted.

As shown in FIG. 4, when the reflective-refractive lens RL is formed in such a way that the condition (2) is satisfied (refer to FIG. 4(*a*)), it is possible to decrease a range in which the second surface RLb$_2$ is formed, as compared with the case where the reflective-refractive lens RL is formed in such a way that the condition (2) is not satisfied (refer to FIG. 4(*b*)).

Also, it is preferred that the optical systems of the present embodiments are formed in such a way that the following condition (3) is satisfied:

$$f_{s\_21\_Mid} < 0 \quad (3)$$

where $f_{s\_21\_Mid}$ denotes the focal length of the reflective-refractive lens relative to light the chief ray of which passes through the middle angle of view in light from the approximately-lateral-object side.

This condition (3) is a condition for prescribing the refractive power of the reflective-refractive lens relative to light from the approximately-lateral-object side. Specifically, this condition (3) is a condition for prescribing that the reflective-refractive lens has negative refractive power relative to light from the approximately-lateral-object side.

The optical systems of the present embodiments are characterized in that the third lens group which is nearer to the image side than the aperture stop has positive refractive power. Also, light from the approximately-lateral-object side does not pass through the first lens group. Accordingly, in order to strike a balance with the positive refractive power of the third lens group, there is necessity that the second lens group is made to have negative refractive power. Accordingly, when the reflective-refractive lens is formed in such a way that the condition (3) is satisfied, the optical systems has a combination of the negative lens group and the positive lens group relative to light from the approximately-lateral-object side, so that it is possible to strike a balance between aberration corrections.

Also, it is preferred that the optical systems of the present embodiments are formed in such a way that the following condition (4) is satisfied:

$$f_{s\_Mid} < f_{s\_Max} \quad (4)$$

where $f_{s\_Mid}$ denotes the focal length of the optical system relative to light the chief ray of which passes through the middle angle of view in light from the approximately-lateral-object side, and $f_{s\_Max}$ denotes the focal length of the optical system relative to light the chief ray of which passes through the maximum angle of view in light from the approximately-lateral-object side.

This condition (4) is a condition for prescribing the focal lengths of the reflective-refractive lens relative to light from the approximately-lateral-object side. More specifically, this condition (4) is a condition for prescribing that the focal length relative to light from an object in the vicinity of the maximum angle of view is longer than the focal length relative to light from an object in the vicinity of the middle angle of view, in the focal lengths of the reflective-refractive lens.

In the case where a side wall which is approximately parallel to the optical axis of light from the front-object side, or the like, is observed as an object on the approximately-lateral side using the optical systems of the present embodiments, an object which is located in the direction of the maximum angle of view relative to the approximately lateral side of the reflective-refractive lens is necessarily more distant from the reflective-refractive lens than an object which is located in the direction of the middle angle of view. Accordingly, when the optical systems are formed in such a way that this condition (4) is satisfied, it is easy to prevent defocus.

The optical systems according to the embodiments 1 to 4 are explained by referring the drawings, below.

Besides, in the sectional views of the optical systems, subscript numerals in $r_1, r_2, \ldots$ and $d_1, d_2, \ldots$ in sectional views of the optical system correspond to surface numbers, 1, 2, ... in numerical data, respectively.

Also, in the numerical data, s denotes the surface number, r denotes the radius of curvature of each surface, d denotes a surface interval, nd denotes the refractive index at d line (which has a wave length of 587.5600 nm), vd denotes the Abbe's number to the d line, K denotes a conical coefficient, and $A_4, A_6, A_8,$ and $A_{10}$ denote aspherical surface coefficients, respectively.

Also, in the aspherical surface coefficients in the numerical data, E denotes a power of ten. For example, "E-10" denotes "ten to the power of minus ten". In addition, the shape of each aspherical surface is expressed by the following equation with aspherical surface coefficients in each embodiment, where Z is taken as a coordinate in the direction along the optical axis, and Y is taken as a coordinate in the direction perpendicular to the optical axis:

$$Z = (Y^2/r)/[1+\{1-(1+K)(Y/r)^2\}^{1/2}] + A_4 Y^4 + A_6 Y^6 + A_8 Y^8 + A_{10} Y^{10} + \ldots$$

Embodiment 1

Figure 5:
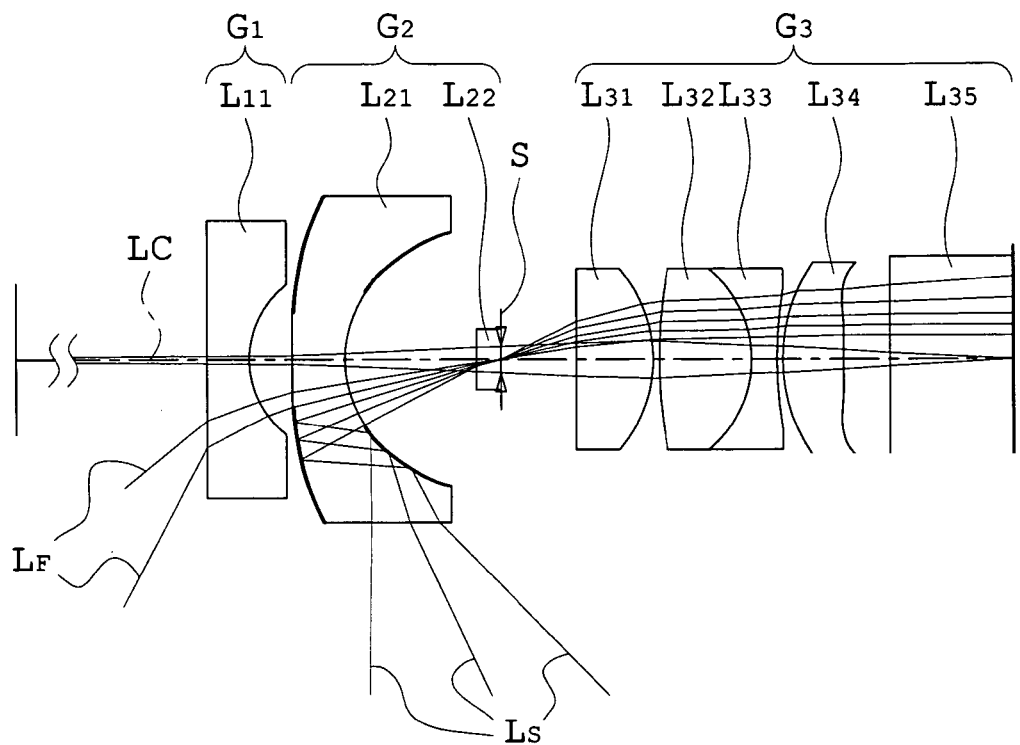
FIG. 5 is a sectional view showing the constitution of the optical system according to the embodiment 1 and optical paths, along the optical axis.
Figure 6:
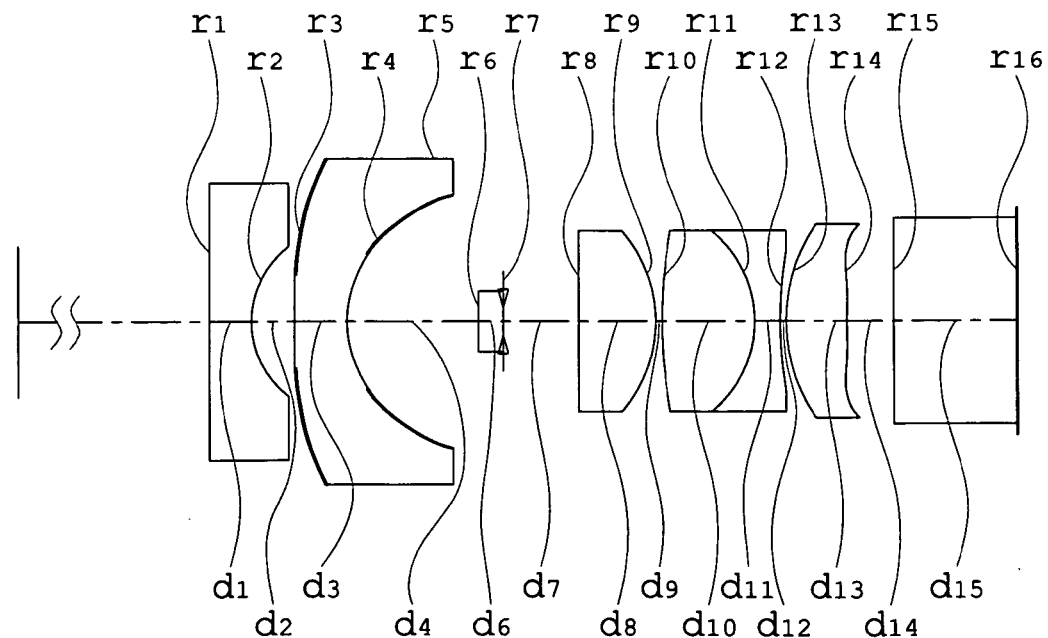
FIG. 6 is a sectional view showing the surfaces of the optical system shown in FIG. 5 and intervals between the surfaces, along the optical axis.

FIG. 5 is a sectional view along the optical axis and shows the constitution of the optical system according to the present embodiment and optical paths. FIG. 6 is a sectional view along the optical axis and shows the surfaces of the optical system shown in FIG. 5 and intervals between the surfaces.

Figure 7:
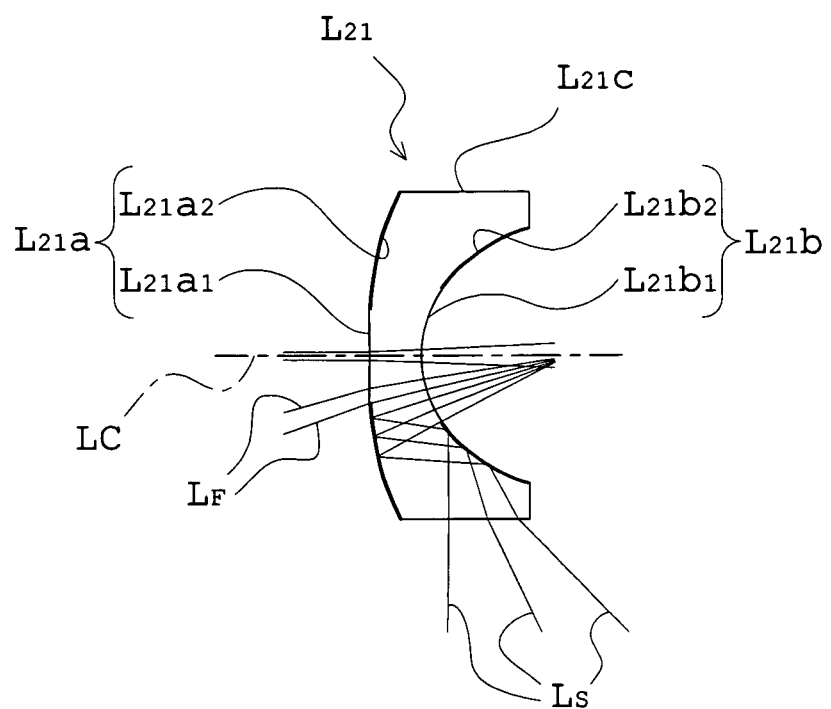
FIG. 7 is an enlarged view of part of the optical system shown in FIGS. 5 and 6 (a reflective-refractive lens in the second lens group).

FIG. 7 is an enlarged view of part of the optical system shown in the present embodiment (a reflective-refractive lens in the second lens group).

Figure 8:
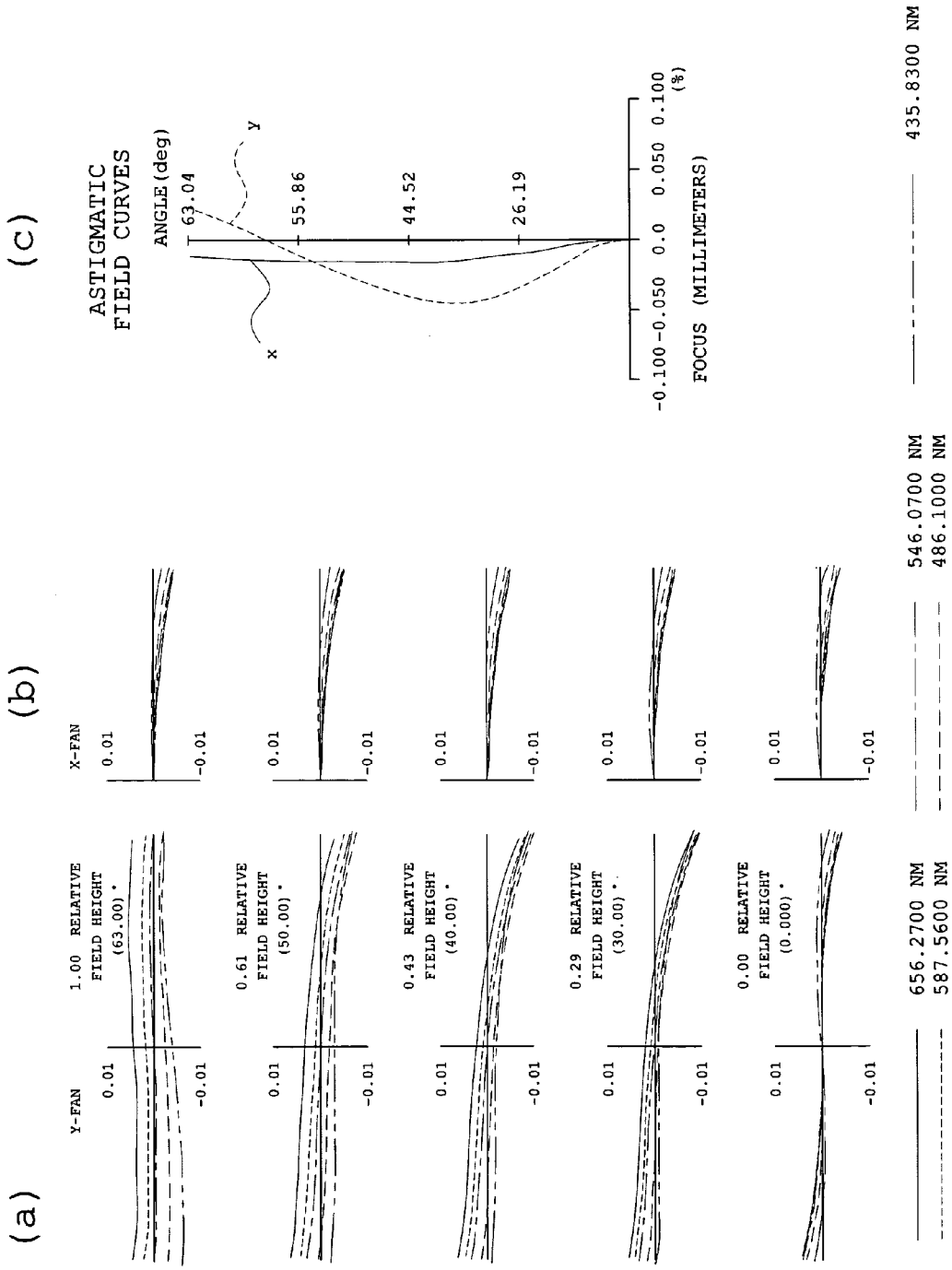
FIG. 8 is a view showing aberration curves in the case where light rays which go from the front-object side to an image plane are traced in the optical system shown in FIGS. 5 to 7, (a) shows coma in a meridional plane, (b) shows coma in a sagittal plane, and (c) shows astigmatism. Also, each of the views shows aberration in the case where a half angle of view is 63°, 50°, 40°, 30°, or 0°, in that order from the top of each of the views.
Figure 9:
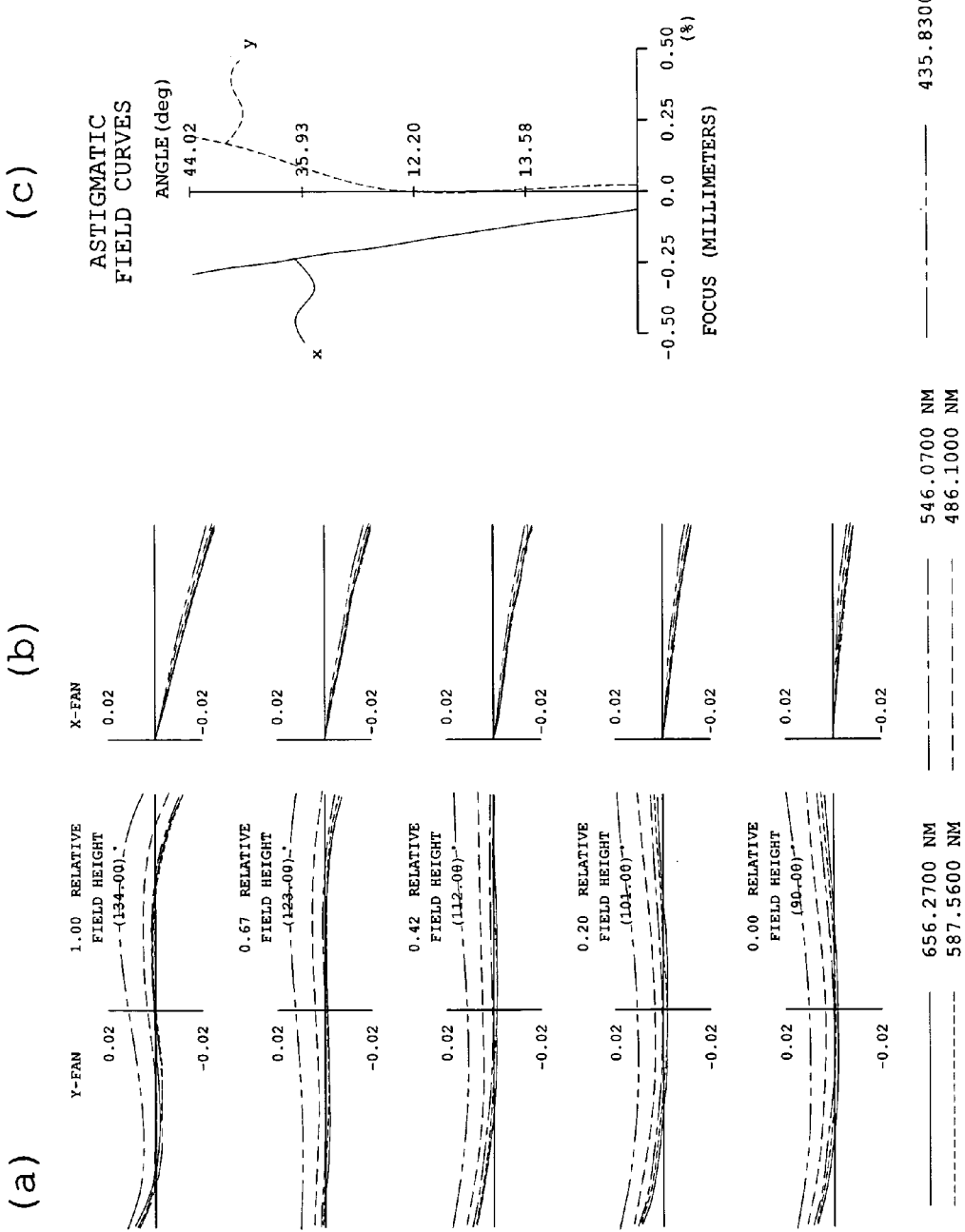
FIG. 9 is a view showing aberration curves in the case where light rays which go from the approximately-lateral-object side to an image plane are traced in the optical system shown in FIGS. 5 to 7, (a) shows coma in a meridional plane, (b) shows coma in a sagittal plane, and (c) shows astigmatism. Also, each of the views shows aberration in the case where a half angle of view is 134°, 123°, 112°, 101°, or 90°, in that order from the top of each of the views.

FIG. 8 is a view showing aberration curves in the case where light rays which go from the front-object side to an image plane are traced in the optical system shown in FIGS. 5 to 7, (a) shows coma in a meridional plane, (b) shows coma in a sagittal plane, and (c) shows astigmatism. Also, each of the views shows aberration in the case where a half angle of view is 63°, 50°, 40°, 30°, or 0°, in that order from the top of each of the views. FIG. 9 is a view showing aberration curves in the case where light rays which go from the approximately-lateral-object side to an image plane are traced in the optical system shown in FIGS. 5 to 7, (a) shows coma in a meridional plane, (b) shows coma in a sagittal plane, and (c) shows astigmatism. Also, each of the views shows aberration in the case where a half angle of view is 134°, 123°, 112°, 101°, or 90°, in that order from the top of each of the views. Besides, the meridional plane means a plane (plane parallel to this document plane) including the optical axis and the chief ray of an optical system. The sagittal plane means a plane (plane perpendicular to this document plane) including the optical axis and perpendicular to the meridional plane. Because the optical system of the present embodiment is symmetric relative to the meridional plane, negative values of aberration amount in the sagittal plane are omitted in the horizontal axis. In the drawings showing coma, the vertical axis denotes aberration amount (unit: mm) and the horizontal axis denotes aperture ratio (ranging from −1 to 1), respectively. Wavelengths which correspond to lines respectively are shown on the right ends of the drawings, respectively. For example, the wavelength which corresponds to a solid line is a wavelength of 656.27 nm. In the drawings showing astigmatism, the vertical axis denotes angle (unit: deg) and the horizontal axis denotes focal position (unit: mm), respectively. Also, the solid line ("y" in the drawing) denotes aberration amount relative to a wavelength of 546.07 nm in the sagittal plane, and the broken line ("x" in the drawing) denotes aberration amount relative to a wavelength of 546.07 nm in the meridional plane.

First, the constitution of the optical system of the present embodiment is explained using FIGS. 5 and 6. In the optical system of the present embodiment, a first lens group $G_1$ with negative refractive power, a second lens group $G_2$, an aperture stop S, and a third lens group $G_3$ with positive refractive power are arranged on the optical axis LC of light from the front-object side and in that order from the front-object side.

The first lens group $G_1$ includes a lens $L_{11}$ which is a plano-concave lens the concave surface of which faces toward the image side, in order from the front-object side.

The second lens group $G_2$ includes a lens $L_{21}$ which is a reflective-refractive lens, and a lens $L_{22}$ which is a flat-plate lens, in that order from the front-object side. Besides, the aperture stop S is arranged on the surface on the image side of the lens $L_{22}$ and integratedly with the lens $L_{22}$.

The third lens group $G_3$ includes a lens $L_{31}$ which is a plano-convex lens the convex surface of which faces toward the image side, a cemented lens, a lens $L_{34}$ which is a biconvex lens the image-side surface of which is an aspherical surface, and a lens $L_{35}$ which is a flat-plate lens, in that order from the front-object side. The cemented lens is composed of a lens $L_{32}$ which is a biconvex lens and a lens $L_{33}$ which is a biconcave lens.

Besides, the shapes of these lenses are shapes in the vicinity of the optical axis of light from the front-object side.

The lens $L_{21}$ which is a reflective-refractive lens includes a first surface $L_{21}a$ which is formed on the front-object side and through which light from the front-object side enters, a second surface $L_{21}b$ which is formed on the image side, and a third surface $L_{21}c$. The third surface $L_{21}c$ is formed on the whole of the peripheral surface between the first surface $L_{21}a$ and the second surface $L_{21}b$, and light from the approximately-lateral-object side enters through the third surface $L_{21}c$.

The first surface $L_{21}a$ includes a first transmission surface $L_{21}a_1$ which is formed with the center of the first transmission surface $L_{21}a_1$ being on the optical axis, and a first reflection surface $L_{21}a_2$ which faces toward the image side and is formed around the first transmission surface $L_{21}a_1$ and in the shape of a ring. The second surface $L_{21}b$ includes a second transmission surface $L_{21}b_1$ which is formed with the center of the second transmission surface $L_{21}b_1$ being on the optical axis, and a second reflection surface $L_{21}b_2$ which faces toward the front-object side and is formed around the second transmission surface $L_{21}b_1$ and in the shape of a ring.

Next, the optical paths which light rays entering the optical system of the present embodiment follow are explained using FIGS. 5 and 7. Light rays $L_F$ which enter the optical system of the present embodiment from the front-object side first pass through the lens $L_{11}$. And, the light rays $L_F$ which have passed through the lens $L_{11}$ enter the first transmission surface $L_{21}a_1$ of the lens $L_{21}$. Afterward, the light rays $L_F$ which have entered the first transmission surface $L_{12}a_1$ emerge from the second transmission surface $L_{21}b_1$ of the lens $L_{21}$. The light rays $L_F$ which have emerged from the second transmission surface $L_{12}b_1$ pass through the lens $L_{22}$, the aperture stop S, the lenses $L_{31}$ to $L_{35}$, in that order, and enter an imaging element or the like.

On the other hand, light rays $L_S$ which enter the optical system of the present embodiment from the approximately-lateral-object side first enter the third surface $L_{21}c$ of the lens $L_{21}$. And, the light rays $L_S$ which have entered the third surface $L_{21}c$ are reflected by the second reflection surface $L_{21}b_2$ of the lens $L_{21}$. Next, the light rays $L_S$ which have been reflected by the second reflection surface $L_{12}b_2$ are reflected by the first reflection surface $L_{21}a_2$ of the lens $L_{21}$. Afterward, the light rays $L_S$ which have been reflected by the first reflection surface $L_{12}a_2$ emerge from the second transmission surface $L_{21}b_1$ of the lens $L_{21}$. The light rays $L_S$ which have emerged from the second transmission surface $L_{12}b_1$ pass through the lens $L_{22}$, the aperture stop s, the lenses $L_{31}$ to $L_{35}$, in that order, and enter the imaging element or the like.

Next, the constitutions and the numerical value data of the lenses which constitute the optical system according to the present embodiment are shown.

Numerical value data 1
Unit: mm
Surface data

| Surface No. s | Radius of curvature r | Surface interval d | Refractive index nd | Abbe's number vd |
|---|---|---|---|---|
| Object plane | ∞ | 8.493 | | |
| 1 | ∞ | 0.7 | 1.8830 | 40.8 |
| 2 | 1.588 | 0.7 | | |
| 3 | −107.841 | 0.85 | 1.5163 | 64.1 |
| (Aspherical surface) | | | | |
| 4 | 2.131 | 2.157 | | |
| (Aspherical surface) | | | | |
| 5 | 2.700 | 2.700 | | |
| 6 | ∞ | 0.4 | 1.5163 | 64.1 |
| 7 | ∞ | 1.234 | | |

-continued

Numerical value data 1
Unit: mm
Surface data

| Surface No. s | Radius of curvature r | Surface interval d | Refractive index nd | Abbe's number vd |
|---|---|---|---|---|
| (Aperture stop) | | | | |
| 8 | ∞ | 1.25 | 1.7725 | 49.6 |
| 9 | −2.330 | 0.1 | | |
| 10 | 8.269 | 1.5 | 1.7292 | 54.7 |
| 11 | −1.967 | 0.4 | 1.8467 | 23.8 |
| 12 | 6.730 | 0.1 | | |
| 13 | 2.85 | 1 | 1.5163 | 64.1 |
| 14 | −8.822 | 0.75 | | |
| (Aspherical surface) | | | | |
| 15 | ∞ | 2 | 1.5163 | 64.1 |
| 16 | ∞ | 0 | | |
| Image plane | ∞ | 0 | | |

Besides, the radius of curvature for the surface No. 5 denotes the radius of curvature of the third surface of the lens $L_{21}$ that is a reflective-refractive lens, or the radius of curvature of a cylinder-shaped surface the center of which is on the optical axis. Also, the surface interval for the surface No. 5 denotes the distance between the optical axis and the surface having the surface No. 5.

Aspherical surface data

| s | r | k | $A_4$ | $A_6$ | $A_8$ | $A_{10}$ |
|---|---|---|---|---|---|---|
| 3 | −107.841 | 0 | 2.62089E−02 | −3.58125E−03 | −6.23702E−06 | 3.69654E−05 |
| 4 | 2.131 | 0 | 1.86065E−02 | −1.38914E−03 | 1.08439E−03 | −4.17585E−04 |
| 14 | −8.822 | 0 | −1.02784E−02 | 4.71739E−02 | −1.54701E−02 | 2.96788E−03 |

The focal length of the whole of optical system (forward): 0.602 mm
F number: 5.6
Half angle of view
  On the front-object side: 70°
  On the approximately-lateral-object side (the minimum angle of view to the maximum angle of view): 90~135°
Image height: 1.35 mm
The total length of lens: 13.14 mm
Back focus: 0 mm
Next, data with respect to the above-described conditions in the optical system of the present embodiment are shown.
  $R_{21\_1}/f_{F\_21}$: 26.826
  $f_{S\_Mid}$: 0.830
  $f_{S\_Max}$: 2.047
  $1/f_{S\_21\_Mid}$: −0.605
  $1/f_{S\_21\_Max}$: −0.204

Embodiment 2

Figure 10:
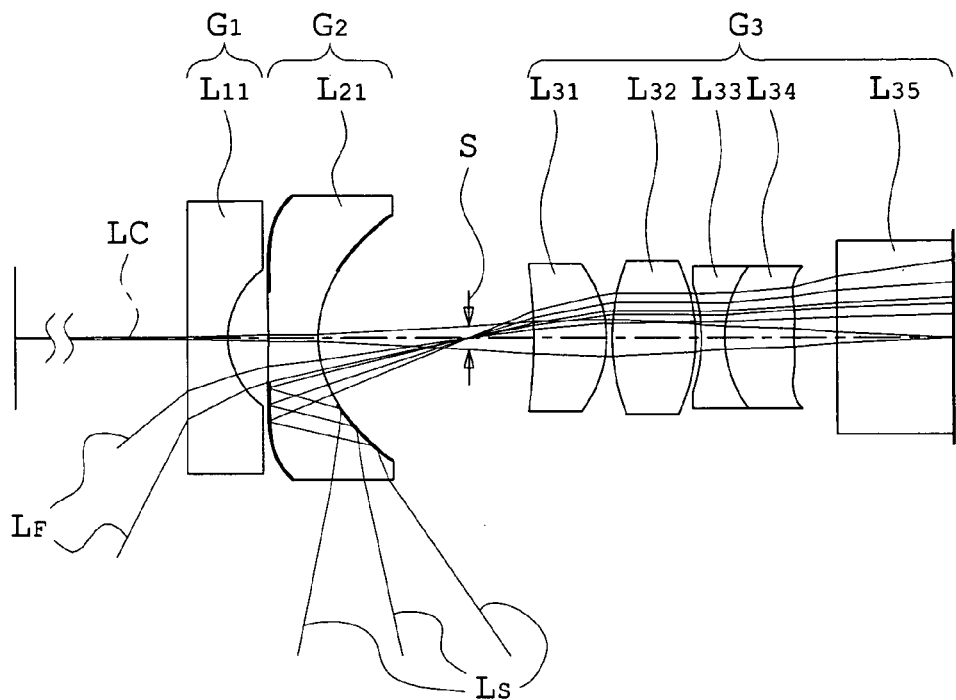
FIG. 10 is a sectional view showing the constitution of the optical system according to the embodiment 2 and optical paths, along the optical axis.
Figure 11:
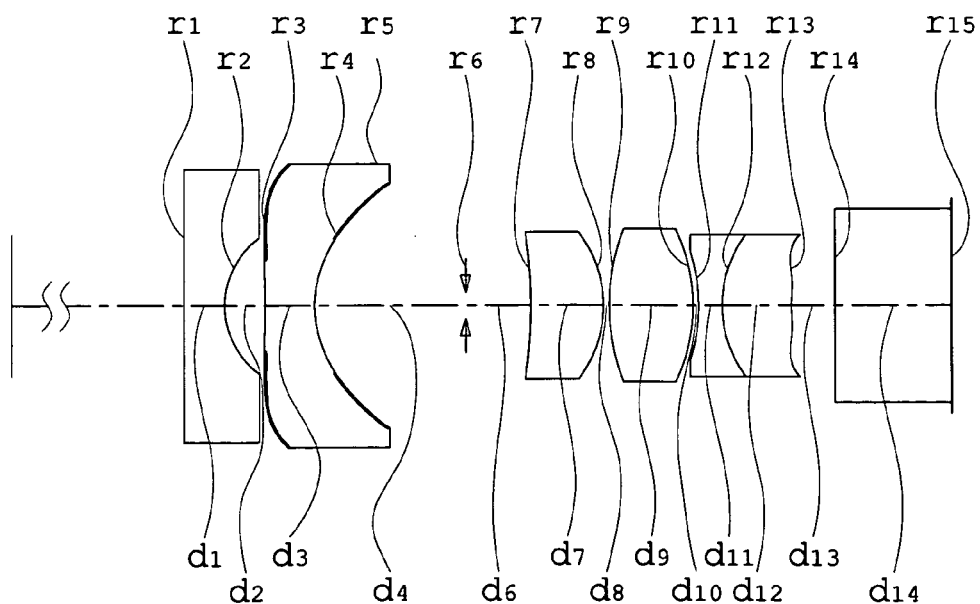
FIG. 11 is a sectional view showing the surfaces of the optical system shown in FIG. 10 and intervals between the surfaces, along the optical axis.

FIG. 10 is a sectional view along the optical axis and shows the constitution of the optical system according to the present embodiment and optical paths. FIG. 11 is a sectional view along the optical axis and shows the surfaces of the optical system shown in FIG. 10 and intervals between the surfaces.

Figure 12:
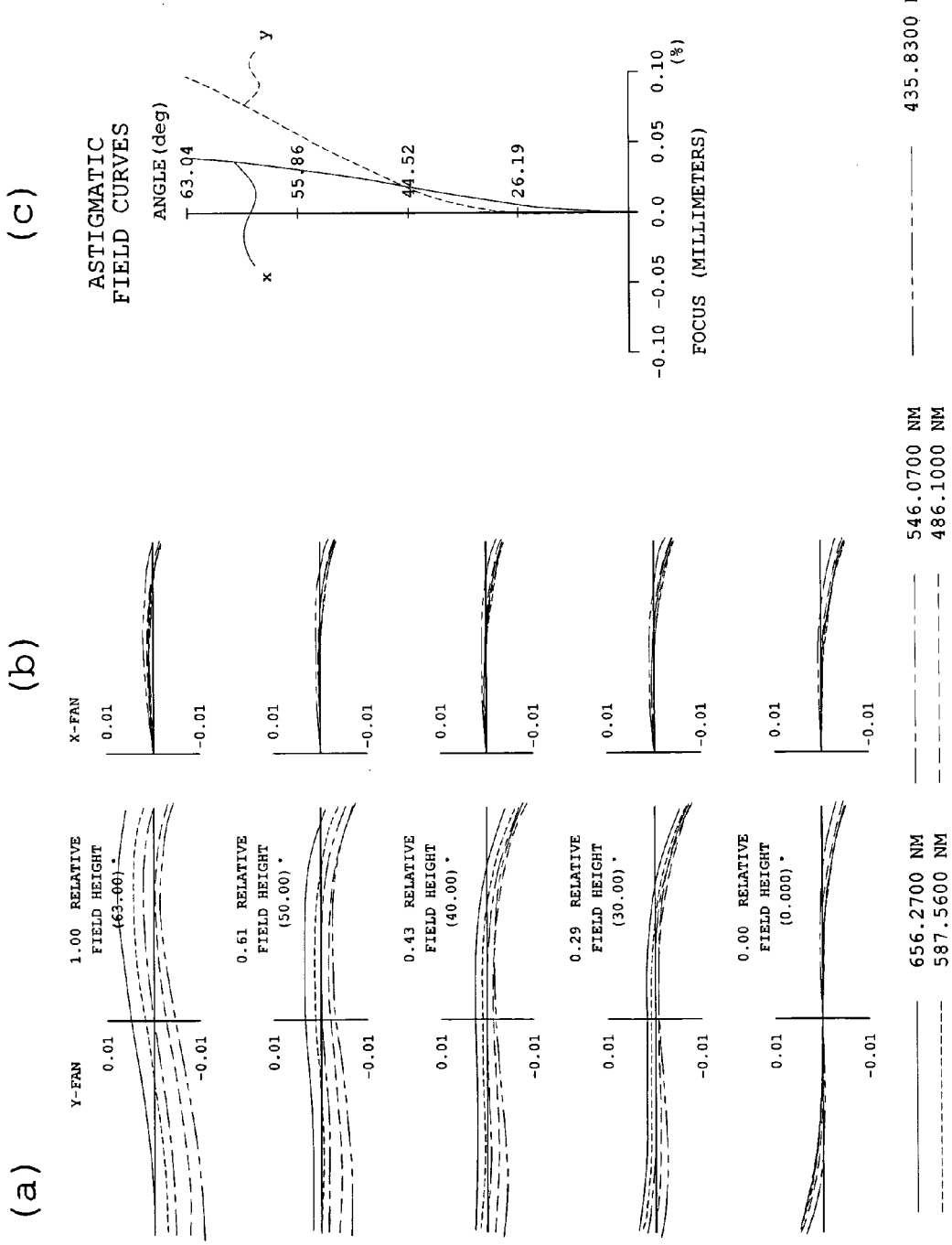
FIG. 12 is a view showing aberration curves in the case where light rays which go from the front-object side to an image plane are traced in the optical system shown in FIGS. 10 and 11, (a) shows coma in a meridional plane, (b) shows coma in a sagittal plane, and (c) shows astigmatism. Also, each of the views shows aberration in the case where a half angle of view is 63°, 50°, 40°, 30°, or 0°, in that order from the top of each of the views.
Figure 13:
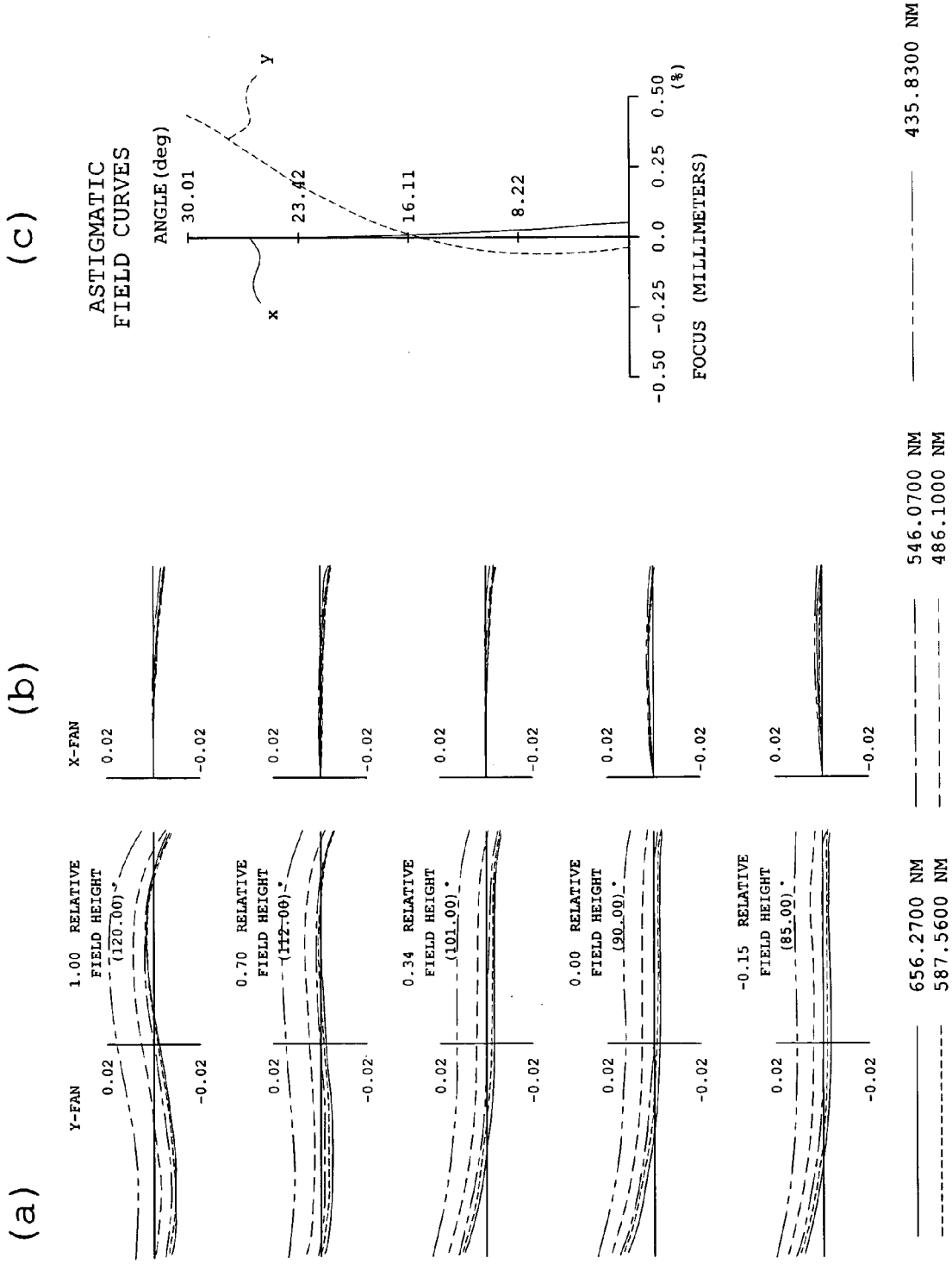
FIG. 13 is a view showing aberration curves in the case where light rays which go from the approximately-lateral-object side to an image plane are traced in the optical system shown in FIGS. 10 and 11, (a) shows coma in a meridional plane, (b) shows coma in a sagittal plane, and (c) shows astigmatism. Also, each of the views shows aberration in the case where a half angle of view is 120°, 112°, 101°, 90°, or 85°, in that order from the top of each of the views.

FIG. 12 is a view showing aberration curves in the case where light rays which go from the front-object side to an image plane are traced in the optical system shown in FIGS. 10 and 11, (a) shows coma in a meridional plane, (b) shows coma in a sagittal plane, and (c) shows astigmatism. Also, each of the views shows aberration in the case where a half angle of view is 63°, 50°, 40°, 30°, or 0°, in that order from the top of each of the views. FIG. 13 is a view showing aberration curves in the case where light rays which go from the approximately-lateral-object side to an image plane are traced in the optical system shown in FIGS. 10 and 11, (a) shows coma in a meridional plane, (b) shows coma in a sagittal plane, and (c) shows astigmatism. Also, each of the views shows aberration in the case where a half angle of view is 120°, 112°, 101°, 90°, or 85°, in that order from the top of each of the views.

First, the constitution of the optical system of the present embodiment is explained using FIGS. 10 and 11. In the optical system of the present embodiment, a first lens group $G_1$ with negative refractive power, a second lens group $G_2$, an aperture stop S, and a third lens group $G_3$ with positive refractive power are arranged on the optical axis LC of light from the front-object side and in that order from the front-object side.

The first lens group $G_1$ includes a lens $L_{11}$ which is a plano-concave lens the concave surface of which faces toward the image side.

The second lens group $G_2$ includes a lens $L_{21}$ which is a reflective-refractive lens.

The third lens group $G_3$ includes a lens $L_{31}$ which is a positive meniscus lens the convex surface of which faces toward the image side, a lens $L_{32}$ which is a biconvex lens, a cemented lens, and a lens $L_{35}$ which is a flat-plate lens, in that order from the front-object side. The cemented lens is composed of a lens $L_{33}$ which is a biconcave lens and a lens $L_{34}$ which is a biconvex lens the image-side surface of which is an aspherical surface, in that order from the front-object side.

Besides, the shapes of these lenses are shapes in the vicinity of the optical axis of light from the front-object side.

In another matters, optical paths and the shape of the reflective-refractive lens in the optical system of the present embodiment are approximately the same as those in the optical system of the embodiment 1. Accordingly, the explanations of these matters are omitted.

Next, the constitutions and the numerical value data of the lenses which constitute the optical system according to the present embodiment are shown.

Numerical value data 2
Unit: mm
Surface data

| Surface No. s | Radius of curvature r | Surface interval d | Refractive index nd | Abbe's number vd |
|---|---|---|---|---|
| Object plane | ∞ | 8.517 | | |
| 1 | ∞ | 0.7 | 1.8830 | 40.8 |
| 2 | 1.498 | 0.7 | | |
| 3 | −8.407 | 0.85 | 1.5163 | 64.1 |
| (Aspherical surface) | | | | |
| 4 | 2.290 | 2.605 | | |
| (Aspherical surface) | | | | |
| 5 | 2.500 | 2.500 | | |
| 6 | ∞ | 1.145 | | |
| (Aperture stop) | | | | |
| 7 | −8.957 | 1.25 | 1.7725 | 49.6 |
| 8 | −2.209 | 0.1 | | |

-continued

Numerical value data 2
Unit: mm
Surface data

| Surface No. s | Radius of curvature r | Surface interval d | Refractive index nd | Abbe's number vd |
|---|---|---|---|---|
| 9 | 3.795 | 1.45 | 1.7292 | 54.7 |
| 10 | −3.196 | 0.1 | | |
| 11 | −3.131 | 0.4 | 1.8467 | 23.8 |
| 12 | 2.098 | 1.2 | 1.5163 | 64.1 |
| 13 (Aspherical surface) | −6.267 | 0.75 | | |
| 14 | ∞ | 2 | 1.5163 | 64.1 |
| 15 | ∞ | 0 | | |
| Image plane | ∞ | 0 | | |

Besides, the radius of curvature for the surface No. 5 denotes the radius of curvature of the third surface of the lens $L_{21}$ that is a reflective-refractive lens, or the radius of curvature of a cylinder-shaped surface the to center of which is on the optical axis. Also, the surface interval for the surface No. 5 denotes the distance between the optical axis and the surface having the surface No. 5.

Aspherical surface data

| s | r | k | $A_4$ | $A_6$ | $A_8$ | $A_{10}$ |
|---|---|---|---|---|---|---|
| 3 | −8.407 | 0 | 4.18039E−02 | −7.90749E−03 | 3.92149E−04 | 6.03174E−05 |
| 4 | 2.290 | 0 | 3.46914E−02 | −2.63649E−02 | 7.09801E−03 | −7.50164E−04 |
| 13 | −6.267 | 0 | 2.07916E−02 | 2.02383E−02 | 4.69558E−02 | −1.46362E−02 |

The focal length of the whole of optical system (forward): 0.610 mm
F number: 5.6
Half angle of view
  On the front-object side: 70°
  On the approximately-lateral-object side (the minimum angle of view to the maximum angle of view): 80~125°
Image height: 1.35 mm
The total length of lens: 13.25 mm
Back focus: 0 mm Next, data with respect to the above-described conditions in the optical system of the present embodiment are shown.
  $R_{21\_1}/f_{F\_21}$: 2.487
  $f_{S\_Mid}$: 0.802
  $f_{S\_Max}$: 1.734
  $1/f_{S\_21\_Mid}$: −0.822
  $1/f_{S\_21\_Max}$: −0.437

Embodiment 3

Figure 14:
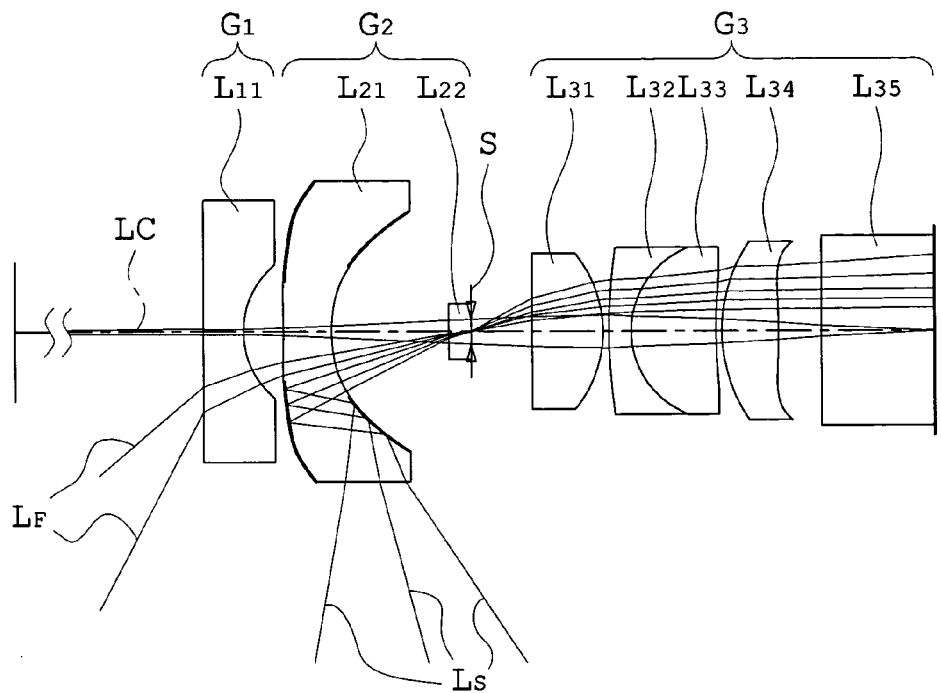
FIG. 14 is a sectional view showing the constitution of the optical system according to the embodiment 3 and optical paths, along the optical axis.
Figure 15:
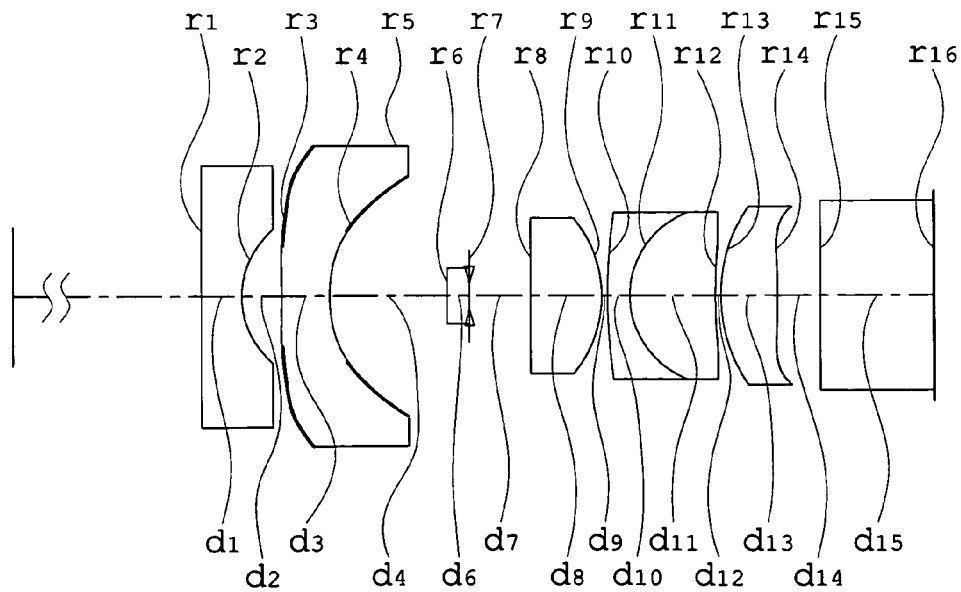
FIG. 15 is a sectional view showing the surfaces of the optical system shown in FIG. 14 and intervals between the surfaces, along the optical axis.

FIG. 14 is a sectional view along the optical axis and shows the constitution of the optical system according to the present embodiment and optical paths. FIG. 15 is a sectional view along the optical axis and shows the surfaces of the optical system shown in FIG. 14 and intervals between the surfaces.

Figure 16:
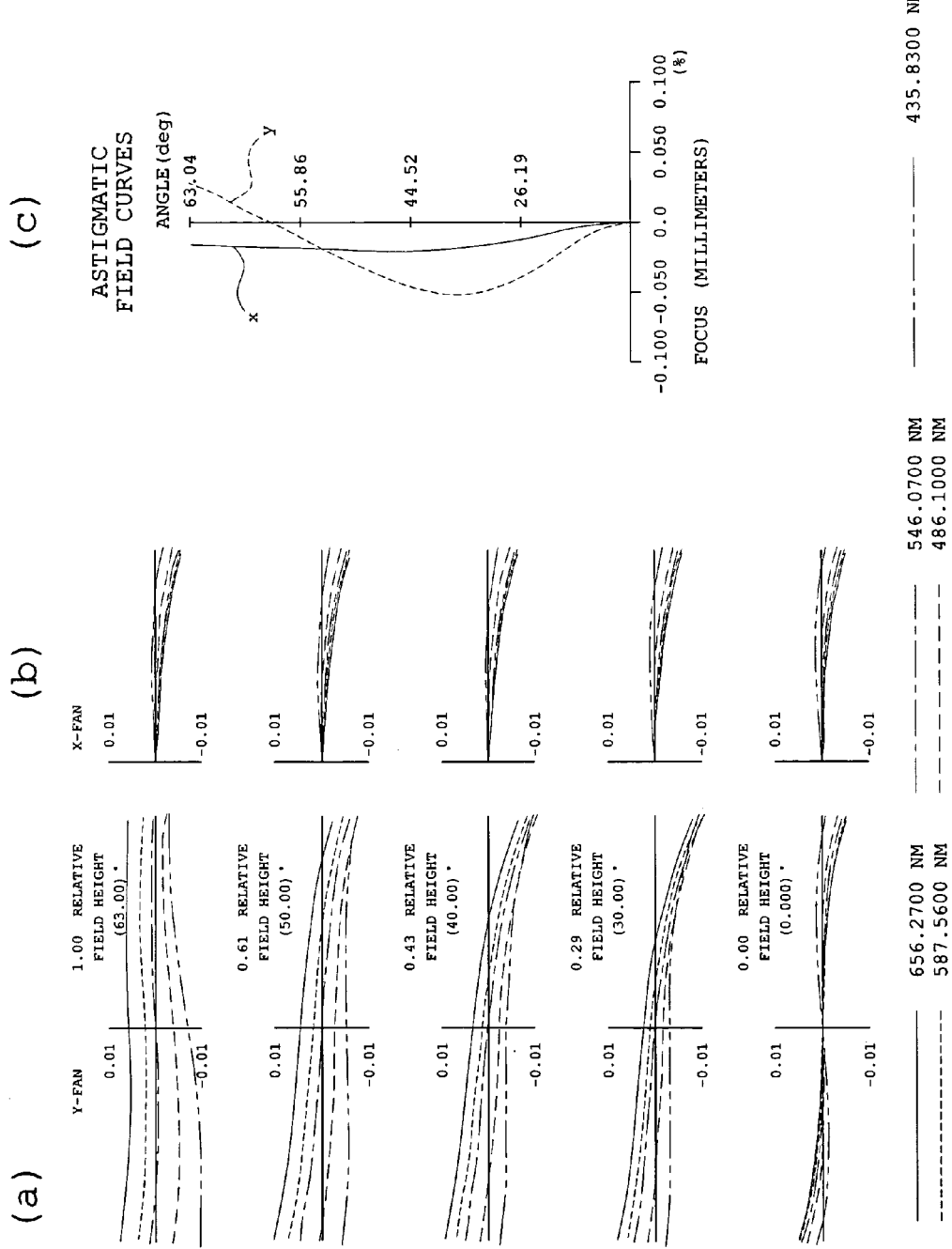
FIG. 16 is a view showing aberration curves in the case where light rays which go from the front-object side to an image plane are traced in the optical system shown in FIGS. 14 and 15, (a) shows coma in a meridional plane, (b) shows coma in a sagittal plane, and (c) shows astigmatism. Also, each of the views shows aberration in the case where a half angle of view is 63°, 50°, 40°, 30°, or 0°, in that order from the top of each of the views.
Figure 17:
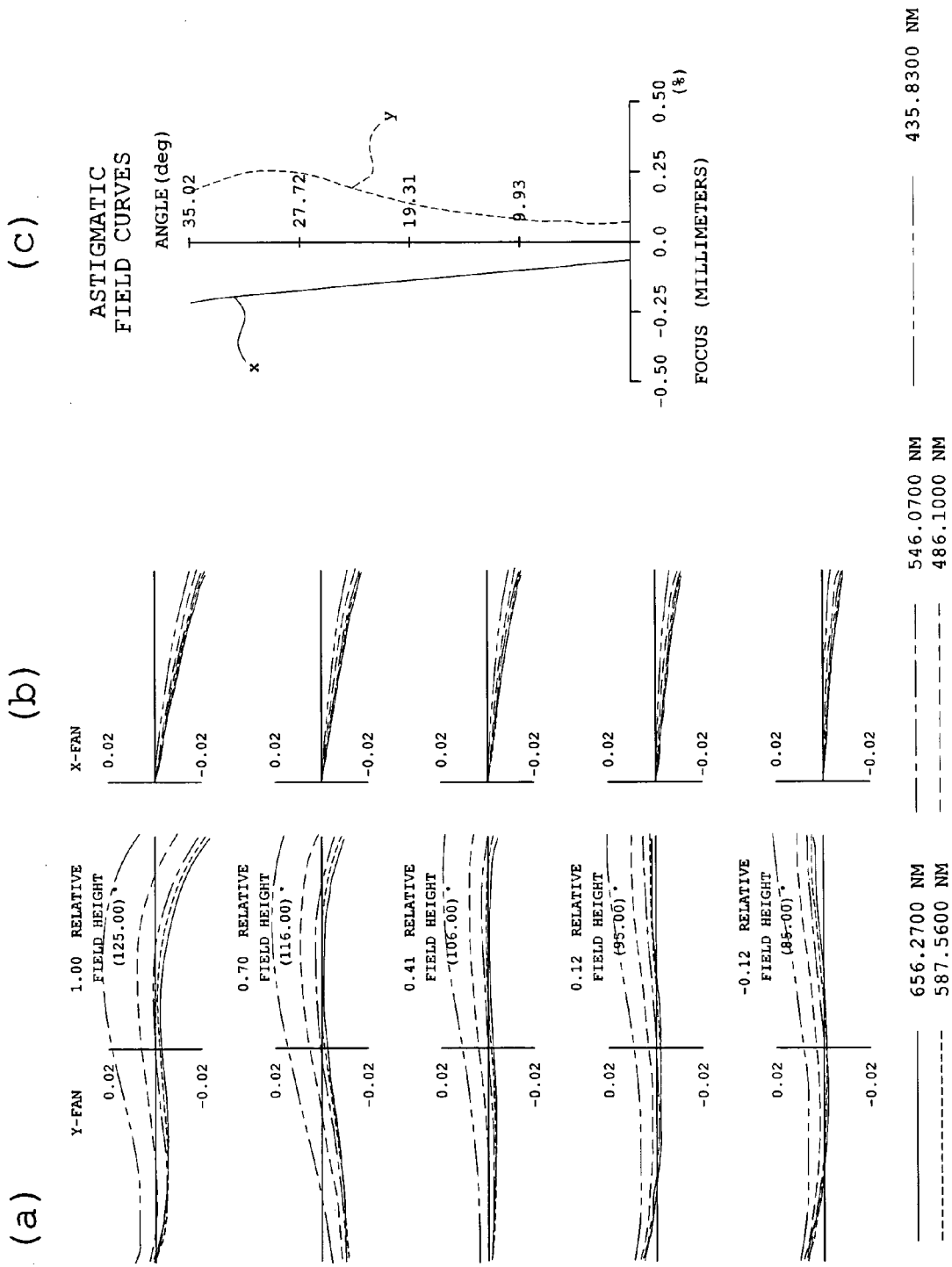
FIG. 17 is a view showing aberration curves in the case where light rays which go from the approximately-lateral-object side to an image plane are traced in the optical system shown in FIGS. 14 and 15, (a) shows coma in a meridional plane, (b) shows coma in a sagittal plane, and (c) shows astigmatism. Also, each of the views shows aberration in the case where a half angle of view is 125°, 116°, 106°, 95°, or 85°, in that order from the top of each of the views.

FIG. 16 is a view showing aberration curves in the case where light rays which go from the front-object side to an image plane are traced in the optical system shown in FIGS. 14 and 15, (a) shows coma in a meridional plane, (b) shows coma in a sagittal plane, and (c) shows astigmatism. Also, each of the views shows aberration in the case where a half angle of view is 63°, 50°, 40°, 30°, or 0°, in that order from the top of each of the views. FIG. 17 is a view showing aberration curves in the case where light rays which go from the approximately-lateral-object side to the image plane are traced in the optical system shown in FIGS. 14 and 15, (a) shows coma in a meridional plane, (b) shows coma in a sagittal plane, and (c) shows astigmatism. Also, each of the views shows aberration in the case where a half angle of view is 125°, 116°, 106°, 95°, or 85°, in that order from the top of each of the views.

First, the constitution of the optical system of the present embodiment is explained using FIGS. 14 and 15. In the optical system of the present embodiment, a first lens group $G_1$ with negative refractive power, a second lens group $G_2$, an aperture stop S, and a third lens group $G_3$ with positive refractive power are arranged on the optical axis LC of light from the front-object side and in that order from the front-object side.

The first lens group $G_1$ includes a lens $L_1$, which is a plano-concave lens the concave surface of which faces toward the image side, in order from the front-object side.

The second lens group $G_2$ includes a lens $L_{21}$ which is a reflective-refractive lens, and a lens $L_{22}$ which is a flat-plate lens the convex surface of which faces toward the front-object side, in that order from the front-object side. The aperture stop S is arranged on the surface on the image side of the lens L22 and integratedly with the lens L22.

The third lens group $G_3$ includes a lens $L_{31}$ which is a plano-convex lens the convex surface of which faces toward the image side, a cemented lens, a lens $L_{34}$ which is a biconvex lens the image-side surface of which is an aspherical surface, and a lens $L_{35}$ which is a flat-plate lens, in that order from the front-object side. The cemented lens is composed of a lens $L_{32}$ which is a negative meniscus lens the convex surface of which faces toward the object side, and a lens $L_{33}$ which is a positive meniscus lens the convex surface of which faces toward the object side, in that order from the front-object side.

Besides, the shapes of these lenses are shapes in the vicinity of the optical axis of light from the front-object side.

In another matters, optical paths and the shape of the reflective-refractive lens in the optical system of the present embodiment are approximately the same as those in the optical systems of the embodiments 1 and 2. Accordingly, the explanations of these matters are omitted.

Next, the constitutions and the numerical value data of the lenses which constitute the optical system according to the present embodiment are shown.

Numerical value data 3
Unit: mm
Surface data

| Surface No. s | Radius of curvature r | Surface interval d | Refractive index nd | Abbe's number vd |
|---|---|---|---|---|
| Object plane | ∞ | 8.464 | | |
| 1 | ∞ | 0.7 | 1.8830 | 40.8 |
| 2 | 1.6 | 0.7 | | |
| 3 (Aspherical surface) | −30.168 | 0.85 | 1.5163 | 64.1 |
| 4 | 2.188 | 2.072 | | |

-continued

Numerical value data 3
Unit: mm
Surface data

| Surface No. s | Radius of curvature r | Surface interval d | Refractive index nd | Abbe's number vd |
|---|---|---|---|---|
| (Aspherical surface) | | | | |
| 5 | 2.700 | 2.700 | | |
| 6 | ∞ | 0.4 | 1.5163 | 64.1 |
| 7 | ∞ | 1.086 | | |
| (Aperture stop) | | | | |
| 8 | ∞ | 1.25 | 1.7725 | 49.6 |
| 9 | −2.247 | 0.1 | | |
| 10 | 9.804 | 0.4 | 1.8467 | 23.8 |
| 11 | 1.618 | 1.5 | 1.7292 | 54.7 |
| 12 | 10.502 | 0.1 | | |
| 13 | 2.857 | 1 | 1.5163 | 64.1 |
| 14 | −16.622 | 0.75 | | |
| (Aspherical surface) | | | | |
| 15 | ∞ | 2 | 1.5163 | 64.1 |
| 16 | ∞ | 0 | | |
| Image plane | ∞ | 0 | | |

Besides, the radius of curvature for the surface No. 5 denotes the radius of curvature of the third surface of the lens $L_{21}$ that is a reflective-refractive lens, or the radius of curvature of a cylinder-shaped surface the center of which is on the optical axis. Also, the surface interval for the surface No. 5 denotes the distance between the optical axis and the surface having the surface No. 5.

| Aspherical surface data | | | | | | |
|---|---|---|---|---|---|---|
| s | r | k | $A_4$ | $A_6$ | $A_8$ | $A_{10}$ |
| 3 | −30.168 | 0 | 2.78649E−02 | −3.89274E−03 | −3.12008E−05 | 4.63052E−05 |
| 4 | 2.188 | 0 | 5.22849E−04 | −6.91877E−04 | 1.51793E−03 | −4.32471E−04 |
| 14 | −16.622 | 0 | −1.47489E−02 | 5.53106E−02 | −2.17956E−02 | 3.97374E−03 |

The focal length of the whole of optical system (forward): 0.596 mm
F number: 5.6
Half angle of view
 On the front-object side: 70°
 On the approximately-lateral-object side (the minimum angle of view to the maximum angle of view): 85~125°
Image height: 1.35 mm
The total length of lens: 12.91 mm
Back focus: 0 mm
Next, data with respect to the above-described conditions in the optical system of the present embodiment are shown.
 $R_{21\_1}/f_{F\_21}$: 7.735
 $f_{S\_Mid}$: 0.798
 $f_{S\_Max}$: 1.961
 $1/f_{S\_21\_Mid}$: −0.646
 $1/f_{S\_21\_Max}$: −0.194

Embodiment 4

Figure 18:
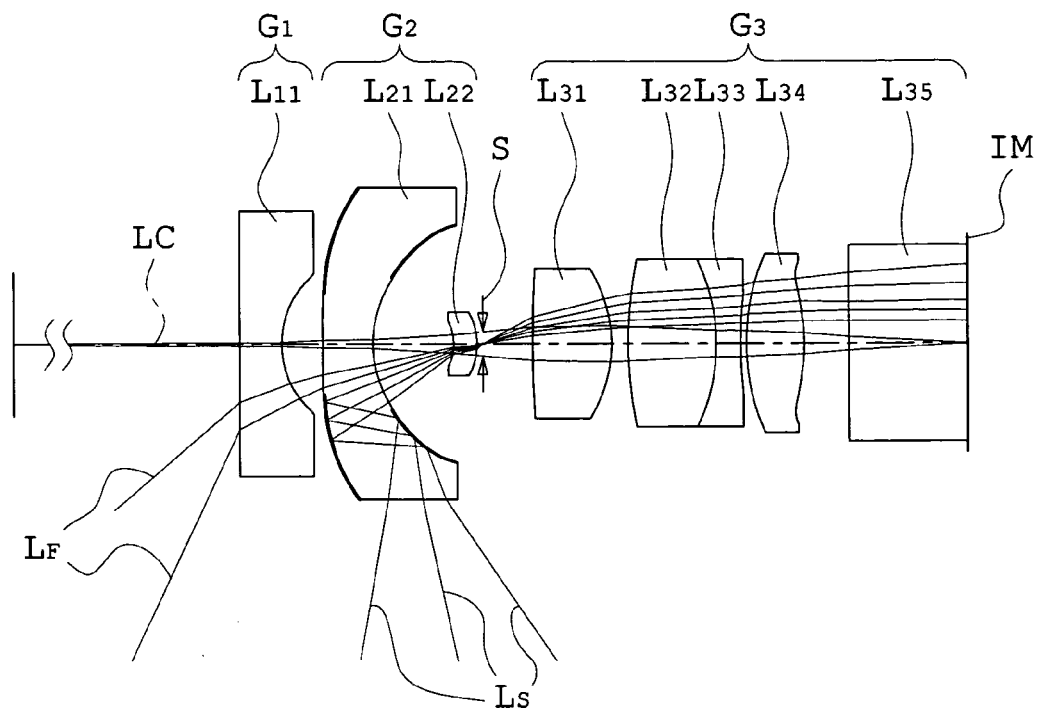
FIG. 18 is a sectional view showing the constitution of the optical system according to the embodiment 4 and optical paths, along the optical axis.
Figure 19:
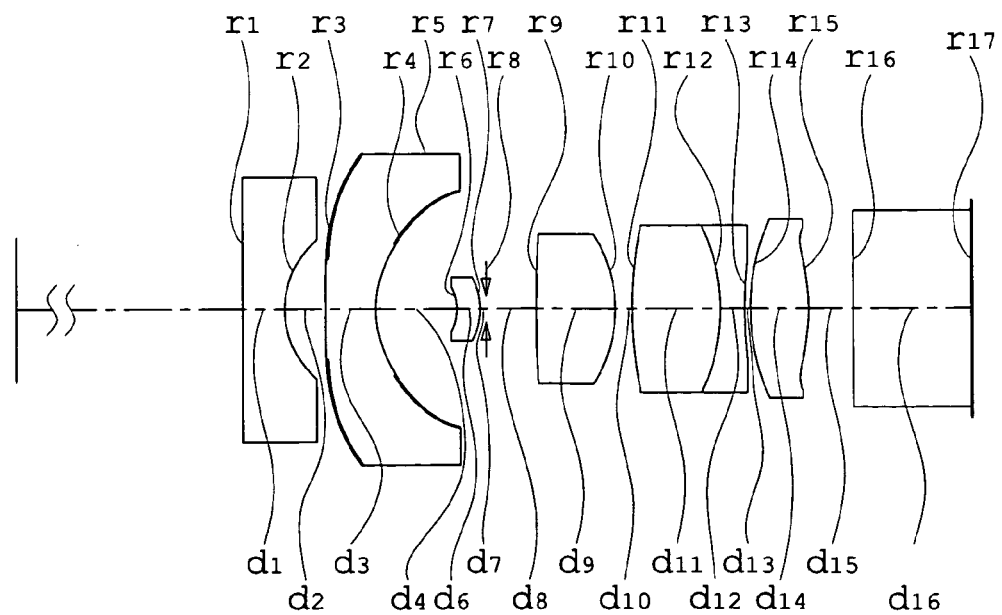
FIG. 19 is a sectional view showing the surfaces of the optical system shown in FIG. 18 and intervals between the surfaces, along the optical axis.
Figure 20:
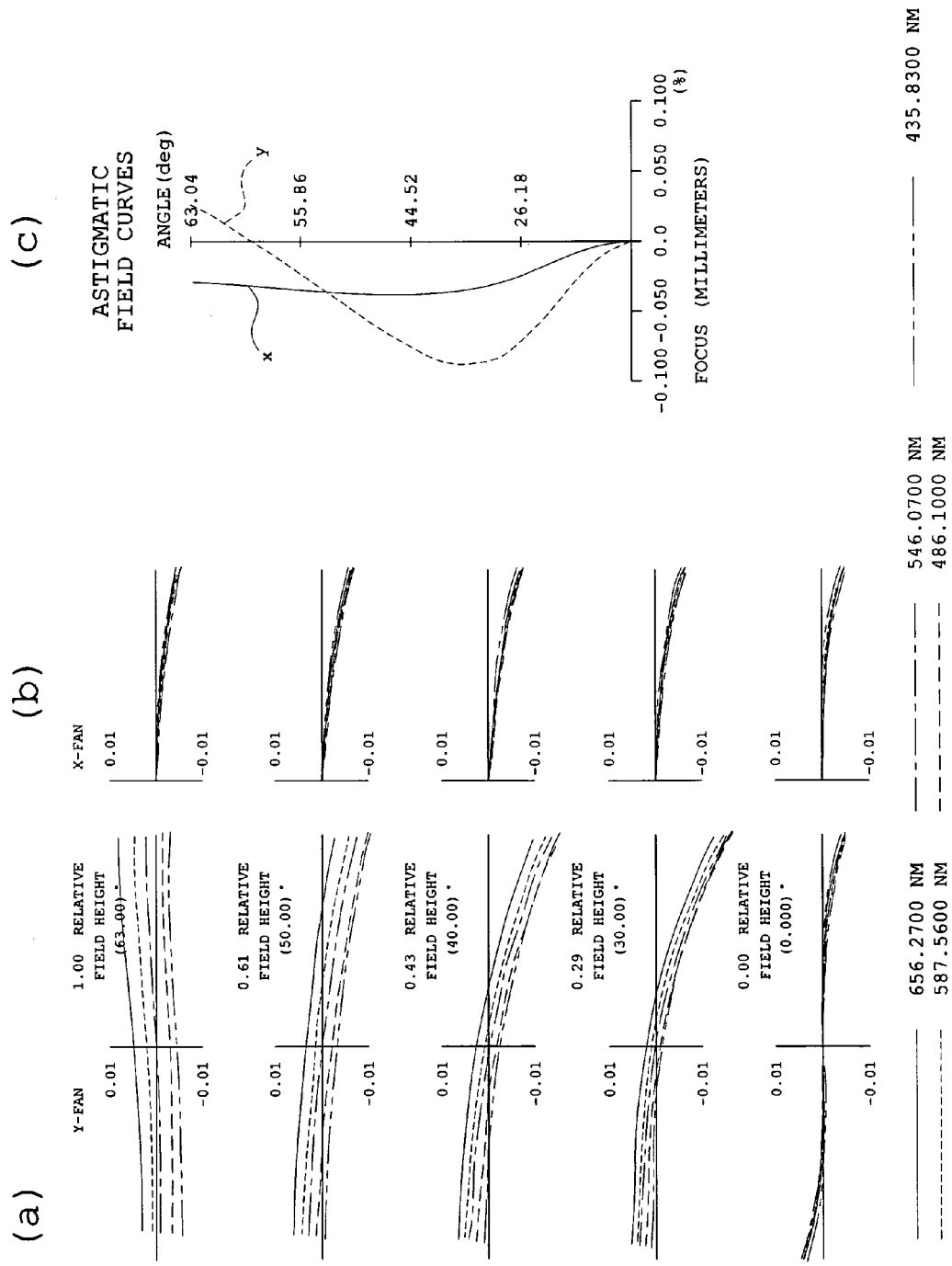
FIG. 20 is a view showing aberration curves in the case where light rays which go from the front-object side to an image plane are traced in the optical system shown in FIGS. 18 and 19, (a) shows coma in a meridional plane, (b) shows coma in a sagittal plane, and (c) shows astigmatism. Also, each of the views shows aberration in the case where a half angle of view is 63°, 50°, 40°, 30°, or 0°, in that order from the top of each of the views.
Figure 21:
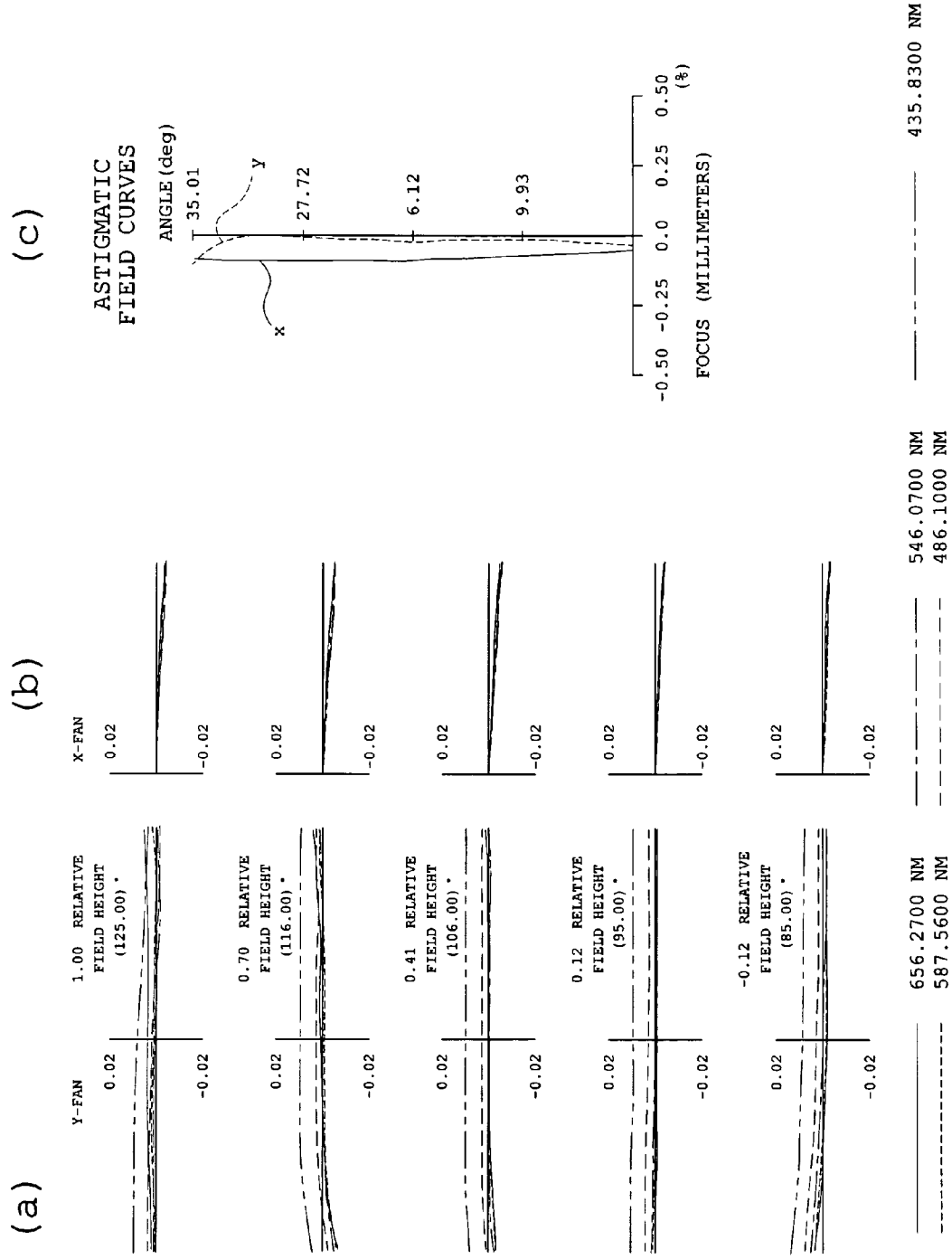
FIG. 21 is a view showing aberration curves in the case where light rays which go from the approximately-lateral-object side to an image plane are traced in the optical system shown in FIGS. 18 and 19, (a) shows coma in a meridional plane, (b) shows coma in a sagittal plane, and (c) shows astigmatism. Also, each of the views shows aberration in the case where a half angle of view is 125°, 116°, 106°, 95°, or 85°, in that order from the top of each of the views.

FIG. 18 is a sectional view along the optical axis and shows the constitution of the optical system according to the present embodiment and optical paths. FIG. 19 is a sectional view along the optical axis and shows the surfaces of the optical system shown in FIG. 18 and intervals between the surfaces. FIG. 20 is a view showing aberration curves in the case where light rays which go from the front-object side to an image plane are traced in the optical system shown in FIGS. 18 and 19, (a) shows coma in a meridional plane, (b) shows coma in a sagittal plane, and (c) shows astigmatism. Also, each of the views shows aberration in the case where a half angle of view is 63°, 50°, 40°, 30°, or 0°, in that order from the top of each of the views. FIG. 21 is a view showing aberration curves in the case where light rays which go from the approximately-lateral-object side to the image plane are traced in the optical system shown in FIGS. 18 and 19, (a) shows coma in a meridional plane, (b) shows coma in a sagittal plane, and (c) shows astigmatism. Also, each of the views shows aberration in the case where a half angle of view is 125°, 116°, 106°, 95°, or 85°, in that order from the top of each of the views.

First, the constitution of the optical system of the present embodiment is explained using FIGS. 18 and 19. In the optical system of the present embodiment, a first lens group $G_1$ with negative refractive power, a second lens group $G_2$, an aperture stop S, and a third lens group $G_3$ with positive refractive power are arranged on the optical axis LC of light from the front-object side and in that order from the front-object side.

The first lens group $G_1$ includes a lens $L_{11}$ which is a plano-concave lens the concave surface of which faces toward the image side, in order from the front-object side.

The second lens group $G_2$ includes a lens $L_{21}$ which is a reflective-refractive lens, and a lens $L_{22}$ which is a negative meniscus lens the convex surface of which faces toward the image side, in that order from the front-object side.

The third lens group $G_3$ includes a lens $L_{31}$ which is a biconvex lens, a cemented lens, a lens $L_{34}$ which is a biconvex lens the image-side surface of which is an aspherical surface, and a lens $L_{35}$ which is a flat-plate lens, in that order from the front-object side. The cemented lens is composed of a lens $L_{32}$ which is a biconvex lens, and a lens $L_{33}$ which is a biconcave lens, in that order from the front-object side.

Besides, the shapes of these lenses are shapes in the vicinity of the optical axis of light from the front-object side.

In another matters, optical paths and the shape of the reflective-refractive lens in the optical system of the present embodiment are approximately the same as those in the optical systems of the embodiments 1 to 3. Accordingly, the explanations of these matters are omitted.

Next, the constitutions and the numerical value data of the lenses which constitute the optical system according to the present embodiment are shown.

Numerical value data 4
Unit: mm
Surface data

| Surface No. s | Radius of curvature r | Surface interval d | Refractive index nd | Abbe's number vd |
|---|---|---|---|---|
| Object plane | ∞ | 8.836 | | |
| 1 | ∞ | 0.7 | 1.8830 | 40.8 |
| 2 | 1.611 | 0.7 | | |
| 3 | −50.750 | 0.85 | 1.5163 | 64.1 |

-continued

Numerical value data 4
Unit: mm
Surface data

| Surface No. s | Radius of curvature r | Surface interval d | Refractive index nd | Abbe's number vd |
|---|---|---|---|---|
| (Aspherical surface) | | | | |
| 4 | 2.179 | 1.396 | | |
| (Aspherical surface) | | | | |
| 5 | 2.700 | 2.700 | | |
| 6 | −0.828 | 0.4 | 1.5163 | 64.1 |
| 7 | −1.161 | 0.1 | | |
| 8 | ∞ | 0.863 | | |
| (Aperture stop) | | | | |
| 9 | 21.240 | 1.35 | 1.8040 | 46.6 |
| 10 | −2.513 | 0.285 | | |
| 11 | 7.223 | 1.5 | 1.7292 | 54.7 |
| 12 | −3.444 | 0.4 | 1.9229 | 18.9 |
| 13 | 7.489 | 0.1 | | |
| 14 | 3.922 | 1 | 1.5163 | 64.1 |
| 15 | −3.548 | 0.75 | | |
| (Aspherical surface) | | | | |
| 16 | ∞ | 2 | 1.5163 | 64.1 |
| 17 | ∞ | 0 | | |
| Image plane | ∞ | 0 | | |

Besides, the radius of curvature for the surface No. 5 denotes the radius of curvature of the third surface of the lens $L_{21}$ that is a reflective-refractive lens, or the radius of curvature of a cylinder-shaped surface the center of which is on the optical axis. Also, the surface interval for the surface No. 5 denotes the distance between the optical axis and the surface having the surface No. 5.

Aspherical surface data

| s | r | k | $A_4$ | $A_6$ | $A_8$ | $A_{10}$ |
|---|---|---|---|---|---|---|
| 3 | −50.750 | 0 | 2.66474E−02 | −3.53765E−03 | 2.86303E−04 | −4.91689E−06 |
| 4 | 2.179 | 0 | 5.85590E−02 | −4.50177E−02 | 1.08714E−02 | −8.24111E−04 |
| 15 | −3.548 | 0 | −4.87606E−02 | 1.36108E−01 | −8.85664E−02 | 2.36820E−02 |

The focal length of the whole of optical system (forward): 0.614 mm
F number: 5.6
Half angle of view
On the front-object side: 70°
On the approximately-lateral-object side (the minimum angle of view to the maximum angle of view): 80~125°
Image height: 1.35 mm
The total length of lens: 12.39 mm
Back focus: 0 mm
Next, data with respect to the above-described conditions in the optical system of the present embodiment are shown.
$R_{21\_1}/f_{F\_21}$: 12.659
$f_{S\_Mid}$: 0.697
$f_{S\_Max}$: 1.414
$1/f_{S\_21\_Mid}$: −0.137
$1/f_{S\_21\_Max}$: 0.824

Embodiment 5

An embodiment of an optical unit which is formed by providing the optical unit with an optical system according to the present invention will be explained in detail, below.

Figure 22:
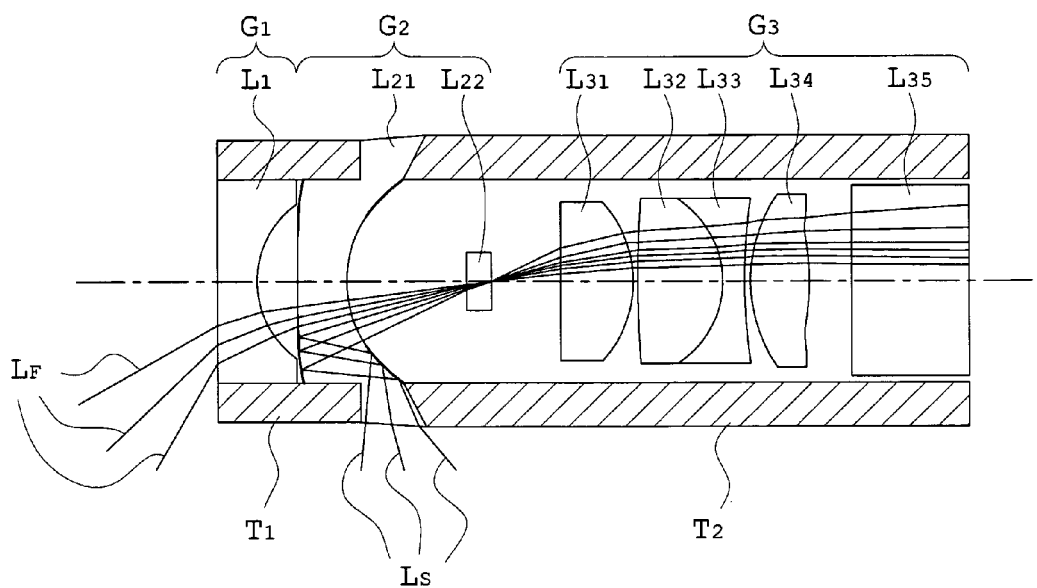
FIG. 22 is a sectional view showing an optical unit using the optical system according to the embodiment 5.

First, the constitution of the optical unit of the present embodiment is explained using FIG. 22. The optical unit of the present embodiment comprises an optical system which consists of three lens groups and by which a front object and an approximately lateral object can be simultaneously observed, and two lens barrels which hold the optical system. Besides, an imaging element like CCD, CMOS, or the like is arranged at the rear of the optical system (on the image side), although the imaging element is not shown in the drawings in the present embodiment. Also, a low pass filter which is given IR cut coating, a CCD-cover glass, or the like is arranged between the optical system and the imaging element.

Because the optical system for the present embodiment by which a front object and an approximately lateral object can be simultaneously observed is approximately the same as the optical systems of the above-described embodiments 1 to 4, the detailed explanations of matters except for the lens $L_{21}$ are omitted.

Figure 23:
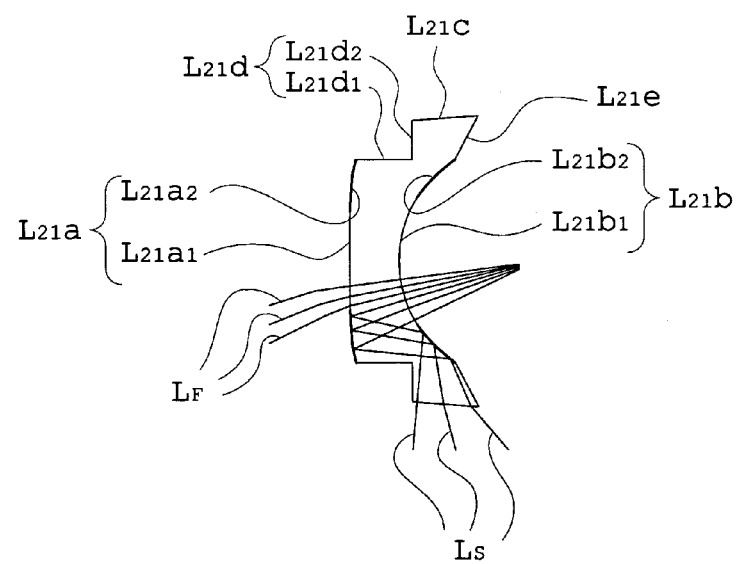
FIG. 23 is a schematic view showing an optical element (reflective-refractive lens) which is included by the optical system that is provided for the optical unit shown in FIG. 22.

As shown in FIG. 23, the lens $L_{21}$ which is an optical element (reflective-refractive lens) for simultaneously observing a front object and an approximately lateral object and has a special shape includes: a first surface $L_{21}a$ which is formed on the front-object side and through which light from the front-object side enters; a second surface $L_{21}b$ which is formed on the image side; and a third surface $L_{21}c$ which is formed on the whole of the peripheral surface between the first surface and the second surface and through which light from the approximately-lateral-object side enters. Also, a first fitting portion $L_{21}d$ is formed between the first surface $L_{21}a$ and the third surface $L_{21}c$ and a second fitting portion $L_{21}e$ is formed between the second surface $L_{21}b$ and the third surface $L_{21}c$.

The first surface $L_{21}a$ of the lens $L_{21}$ includes: a first transmission surface $L_{21}a_1$ which is formed with the center of the first transmission surface $L_{21}a_1$ being on the optical axis; and a first reflection surface $L_{21}a_2$ which faces toward the image side and is formed around the first transmission surface $L_{21}a_1$ and in the shape of a ring. The second surface $L_{21}b$ includes: a second transmission surface $L_{21}b_1$ which is formed with the center of the second transmission surface $L_{21}b_1$ being on the optical axis; and a second reflection surface $L_{21}b_2$ which faces toward the front-object side and is formed around the second transmission surface $L_{21}b_1$ and in the shape of a ring. Besides, in the present embodiment, the third surface $L_{21}c$ is formed in such a way that the image-side diameter of the third surface $L_{21}c$ is larger than the front-object-side diameter of the third surface $L_{21}c$. However, the third surface $L_{21}c$ may be formed in such a way that the image-side diameter of the third surface $L_{21}c$ is smaller than the front-object-side diameter of the third surface $L_{21}c$. In this case, "the front-object-side diameter" means "the diameter in the surface which is located at the position nearest to the front-object side in the third surface $L_{21}c$ and is perpendicular to the optical axis". Also, "the image-side diameter" means "the diameter in the surface which is located at the position nearest to the image side in the third surface $L_{21}c$ and is perpendicular to the optical axis".

Also, a first fitting portion $L_{21}d$ is formed around the first reflection surface $L_{21}a_2$ of the first surface $L_{21}a$ of the lens $L_{21}$. The first fitting portion $L_{21}d$ is fitted to a first lens barrel $T_1$, as shown in FIG. 1. Besides, the first fitting portion $L_{21}d$ is formed by a cylindrical surface $L_{21}d_1$ the center of which is on the optical axis and an annular surface $L_{21}d_2$ which is approximately perpendicular to the optical axis, in such a way that the first fitting portion $L_{21}d$ is formed annularly and in the shape of a step. On the other hand, a second fitting portion $L_{21}e$ to which a second lens barrel $T_2$ holding the second lens group $G_2$ is fitted as shown in FIG. 1 is formed around the second reflection surface to $L_{21}b_2$ of the second surface $L_{21}b$ of the lens $L_{21}$. As described above, in the optical unit of the present embodiment, the fitting portion for fitting the lens barrel is formed in the lens $L_{21}$ which is an optical system for simultaneously observing a front object and an approximately lateral object, so that there is no necessity for providing an optical unit with a holding member that is larger than the diameters of lenses of its optical system as in conventional optical units. In this case, the first lens barrel $T_1$, the lens $L_{21}$, and the second lens barrel $T_2$ are arranged in such a way that each of the first lens barrel $T_1$, the lens $L_{21}$, and the second lens barrel $T_2$ is rotationally symmetric relative to the optical axis. In addition, the first fitting portion $L_{21}d$ is also formed in such a way that the first fitting portion $L_{21}d$ is rotationally symmetric relative to the optical axis.

The optical system which constitutes the optical unit of the present embodiment is the same as the optical systems in the embodiments 1 to 4. Its second lens group $G_2$ includes the lens $L_{21}$. And, this lens $L_{21}$ is an optical element (reflective-refractive lens) having the first reflection surface $L_{21}a_2$ and the second reflection surface $L_{21}b_2$. Accordingly, as a result of making the lens $L_{21}$ with sufficient precision, the relation between the two reflection surfaces arranged also has sufficient precision, so that it is possible to prevent the first reflection surface $L_{21}a_2$ from becoming eccentric to the second reflection surface $L_{21}b_2$ in assembling the optical unit. As a result, in optical units for which optical elements (reflective-refractive lens) like the lens $L_{21}$ in the present embodiment are used, it is hard for one member (the first reflection surface $L_{21}a_2$) to become eccentric to the other member (the second reflection surface $L_{21}b_2$), unlike the prior art, and it is possible to prevent the deterioration of a capability of forming an image.

Also, every one of the first lens barrel $T_1$, the lens $L_{21}$, and the second lens barrel $T_2$ is arranged in such a way that the every one is rotationally symmetric to the optical axis. As a result, the optical axes of the first lens group $G_1$ held by the first lens barrel $T_1$, the second lens group $G_2$ including the lens $L_{21}$, and the second lens group $G_2$ held by the second lens barrel $T_2$ can be easily made to correspond with one another in assembling the optical unit. Accordingly, it is possible to prevent a plurality of the lenses from becoming eccentric to one another, and it is possible to prevent the deterioration of the capability of forming an image.

Also, the first fitting portion $L_{21}d$ is also formed in such a way that the first fitting portion $L_{21}d$ is rotationally symmetric to the optical axis. Accordingly, an adjustment of eccentricity is easily made while the first lens barrel $T_1$ and the lens $L_{21}$ are being rotated about the optical axis in assembling the optical unit. Accordingly, in the optical unit of the present embodiment, it is hard for the first lens barrel $T_1$ and the lens $L_{21}$ to become eccentric to each other, and it is possible to prevent the deterioration of the capability of forming an image due to eccentricity.

Besides, in the above-described embodiment 5, two lens barrels are fitted to fitting portions which are formed in an optical element (reflective-refractive lens), respectively. However, the two lens barrels $T_1$ and $T_2$ may be fitted directly to the non-reflection surfaces on the back sides of the reflection surfaces of the lens $L_{21}$ that is the optical element, respectively, without forming the fitting portions in the optical element.

Figure 24:
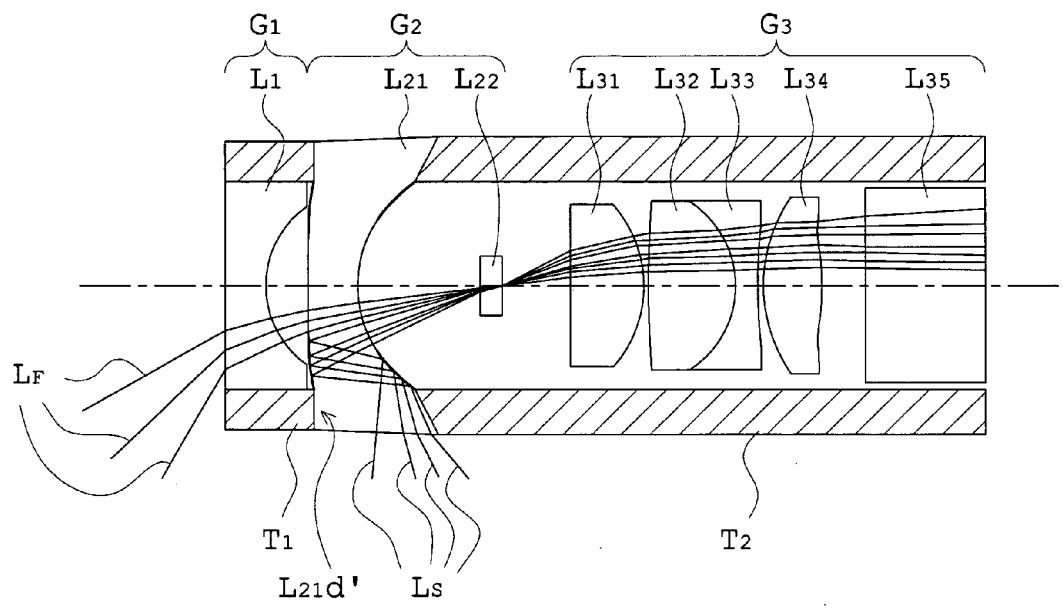
FIG. 24 is a schematic view showing a variation of the optical unit according to the embodiment 5 of the present invention.

Also, in the above-described embodiment 5, the first fitting portion $L_{21}d$ is formed in the shape of a step. However, there is not necessity to necessarily form the first fitting portion $L_{21}d$ in such a shape. For example, like a first fitting portion $L_{21}d'$ in a variation of the optical unit according to the present invention which is shown in FIG. 24, a first fitting portion may be formed in such a way that the object-side surface of the first fitting portion has no difference in level from the first surface $L_{21}a$.

Figure 25:
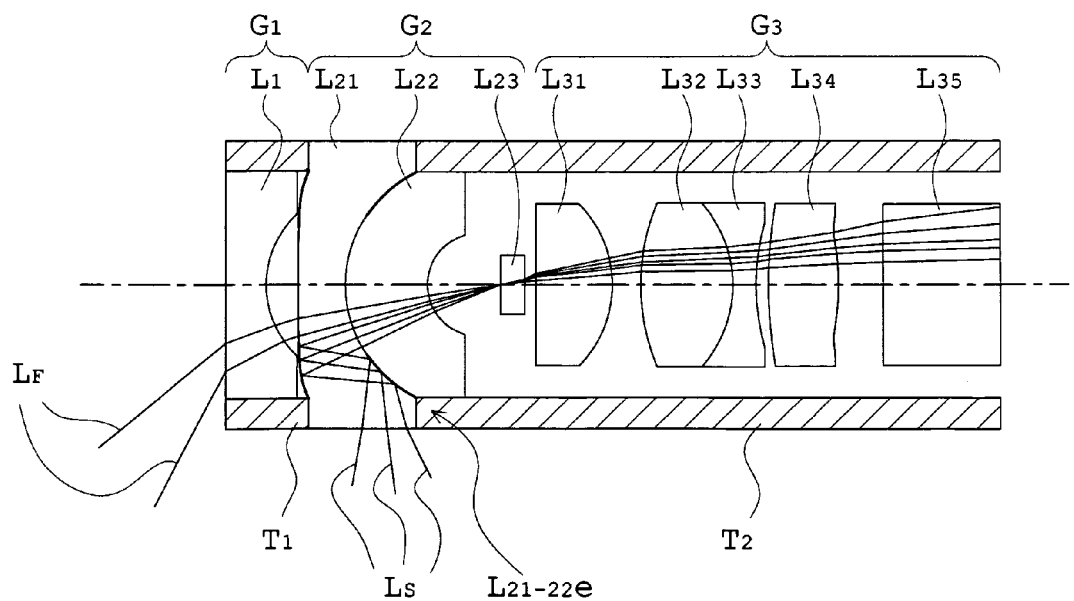
FIG. 25 is a schematic view showing a variation of the optical unit according to the embodiment 5 of the present invention.

Also, in the above-described embodiment 5, the step-shaped first fitting portion $L_{21}d$ is formed on the front-object side of the optical element (caradioptric lens). However, there is not necessity to necessarily form such a fitting portion on the front-object side of the optical element. As in a variation of the optical unit according to the present invention which is shown in FIG. 25, an optical element may be composed of the lens $L_{21}$ and the lens $L_{22}$ which are included by the second lens group $G_2$, so that a step-shaped second fitting portion $L_{21-22}e$ is formed on the image side of the optical element.

Besides, in this variation, the second fitting portion $L_{21-22}e$ is formed in such a way that the second fitting portion $L_{21-22}e$ is rotationally symmetric to the optical axis. As a result, the second lens barrel $T_2$ and the optical element can be easily touched to each other to be assembled. Accordingly, in the optical unit of the present variation, it is hard for both of them to become eccentric, and it is possible to prevent the deterioration of the capability of forming an image due to eccentricity.

Also, in this variation, the step-shaped second fitting portion $L_{21-22}e$ is formed on the image side of the optical element (reflective-refractive lens) by making the optical element of two lenses. However, by the use of the same method as the above-described method of forming the first fitting portion $L_{21}d$ in the embodiment 5, a step-shaped second fitting portion may be formed in one lens, for example, only in the lens $L_{21}$.

Figure 26:
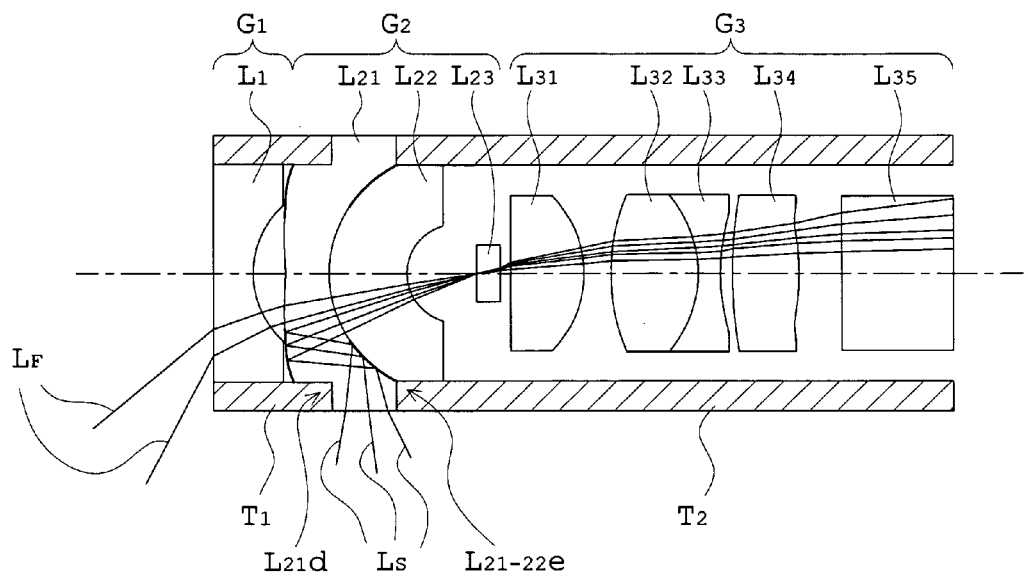
FIG. 26 is a schematic view showing a variation of the optical unit according to the embodiment 5 of the present invention.

Also, in the above-described embodiment 5 and variation, the step-shaped fitting portion is formed only on either of the object side or the image side of the optical element (reflective-refractive lens). However, like the first fitting portion $L_{21}d$ and the second fitting portion $L_{21-22}e$ in a variation of the optical unit according to the present invention which is shown in FIG. 26, fitting portions may be formed in the both surfaces of the optical element.

Besides, in this variation, every one of the first fitting portion $L_{21}d$ and the second fitting portion $L_{21-22}e$ is formed in such a way that the every one is rotationally symmetric to the optical axis. As a result, the first lens barrel $T_1$ and the second lens barrel $T_2$ can be easily touched to the first fitting portion $L_{21}d$ and the second fitting portion $L_{21-22}e$ of the optical element (reflective-refractive lens) respectively to be assembled. Accordingly, in the optical unit of the present variation, it is hard for the optical element, the first lens barrel $T_1$, and the second lens barrel $T_2$ to become eccentric, and it is possible to prevent the deterioration of the capability of forming an image due to eccentricity.

Figure 27:
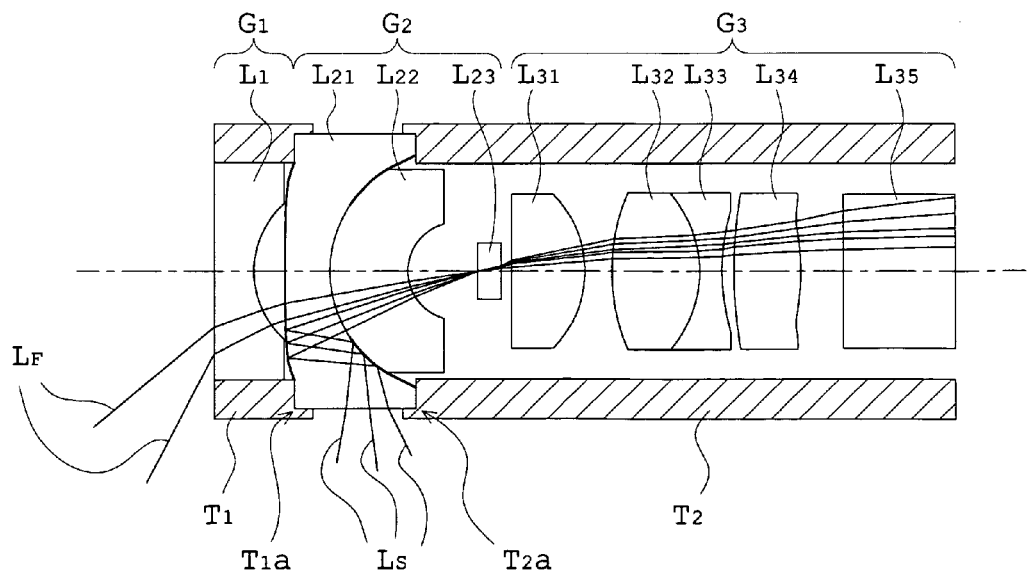
FIG. 27 is a schematic view showing a variation of the optical unit according to the embodiment 5 of the present invention.

Also, in the above-described embodiment 5 and variation, the fitting portion is formed in the optical element (reflective-refractive lens). However, instead of forming the fitting portion in the optical element, a holding portion may be formed in one of or both of a surface of the first lens barrel which is fitted to the first surface of the optical element and a surface of the second lens barrel which is fitted to the second surface of the optical element. For example, as in a variation of the optical unit according to the present invention which is shown in FIG. 27, a first holding portion $T_1a$ may be formed on the edge of the first lens barrel $T_1$ on the lens-$L_{21}$ side, and a second holding portion $T_2a$ may be formed on the edge of the second lens barrel $T_2$ on the front-object side.

Besides, in this variation, the first holding portion $T_1a$ and the second holding portion $T_2a$ are formed in the shape of a step and in such a way that the first holding portion $T_1a$ and the second holding portion $T_2a$ are rotationally symmetric to the optical axis. As a result, the first holding portion $T_1a$ and the second holding portion $T_2a$ can be easily touched to the optical element to be assembled. Accordingly, in the optical unit of the present variation, it is hard for the optical element, the first lens barrel $T_1$, and the second lens barrel $T_2$ to become eccentric, and it is possible to prevent the deterioration of the capability of forming an image due to eccentricity.

Besides, the present invention is not limited to these examples, and the present invention also includes various combinations of the above-described embodiments and variations.

Also, in the above-described embodiments and variations, the third surface $L_{21}c$ of the lens $L_{21}$ that is a reflective-refractive lens is not limited to a surface that is formed on the whole of the peripheral surface between the first surface $L_{21}a$ and the second surface $L_{21}b$. The third surface $L_{21}c$ may be formed on a part of the surface in the circumferential direction so that the optical axis is surrounded by the third surface $L_{21}c$.

Also, lenses which constitute lens groups of optical systems of the present invention are not limited to the shapes and the number of the lenses which are described in the above-described embodiments, and the present invention also includes various optical systems including reflective-refractive lenses.

Also, in the above-described embodiments and variations, the optical systems are composed of three lens groups. However, optical systems of the present invention are not limited to these examples, and the optical systems may be composed of two lens groups or composed of four or more lens groups.

INDUSTRIAL APPLICABILITY

Optical systems of the present invention can restrain the deterioration of the capability of forming an image, so that the optical systems can be preferably used for optical apparatuses such as endoscopes and are extremely useful for practical use.

The invention claimed is:

1. An optical system for observing a front object and an approximately lateral object, wherein
a first lens group with negative refractive power, a second lens group including a reflective-refractive lens, an aperture stop, and a third lens group with positive refractive power are arranged in that order from a front-object side,
the reflective-refractive lens is provided with a first face arranged on the front-object side, a second face arranged on an image side, and a third face formed between the first face and the second face in a circumferential direction to surround an optical axis,
the first face includes a first transmission surface formed with a center of the first transmission surface on the optical axis and a first reflection surface facing toward the image side and formed around the first transmission surface, and the first face is an aspherical surface that is shaped to be smooth and concave toward the object side in a vicinity of the optical axis where the first transmission surface is located, with a center of concavity being on the optical axis, and that is shaped to be convex toward the object side in a region farther from the optical axis, where the first reflection surface is located,
the second face includes a second transmission surface formed with a center of the second transmission surface on the optical axis and a second reflection surface facing toward the front-object side and formed around the second transmission surface, and
the third face is configured as a transmission surface.

2. The optical system according to claim 1, wherein
after light from the front-object side is incident on the first transmission surface, the light emerges from the second transmission surface to the image side, and
after light from an approximately-lateral-object side is incident on the third face, the light is reflected by the second reflection surface and the first reflection surface in that order and emerges from the second transmission surface to the image side.

3. An optical system for observing a front object and an approximately lateral object, wherein
a first lens group with negative refractive power, a second lens group including a reflective-refractive lens, an aperture stop, and a third lens group with positive refractive power are arranged in that order from a front-object side,
the reflective-refractive lens is provided with a first face arranged on the front-object side, a second face arranged on an image side, and a third face formed between the first face and the second face in a circumferential direction to surround an optical axis,
the first face includes a first transmission surface formed with a center of the first transmission surface on the optical axis and a first reflection surface facing toward the image side and formed around the first transmission surface, and the first face is an aspherical surface that has a concave-surface shape in a vicinity of the optical axis and a convex-surface shape in a vicinity of the first reflection surface,
the second face includes a second transmission surface formed with a center of the second transmission surface on the optical axis and a second reflection surface facing toward the front-object side and formed around the second transmission surface,
the third face is configured as a transmission surface, and
the following condition is satisfied:

$$2 < R_{21\_1}/f_{F\_21} < 30$$

where $f_{F\_21}$ denotes a focal length of the reflective-refractive lens for paraxial light rays included in light from the front-object side, and $R_{21\_1}$ denotes a paraxial radius of curvature of the first face of the reflective-refractive lens.

4. An optical system for observing a front object and an approximately lateral object, wherein
a first lens group with negative refractive power, a second lens group including a reflective-refractive lens, an aperture stop, and a third lens group with positive refractive power are arranged in that order from a front-object side,
the reflective-refractive lens is provided with a first face arranged on the front-object side, a second face arranged on an image side, and a third face formed between the first face and the second face in a circumferential direction to surround an optical axis,
the first face includes a first transmission surface formed with a center of the first transmission surface on the optical axis and a first reflection surface facing toward the image side and formed around the first transmission surface, and the first face is an aspherical surface that has a concave-surface shape in a vicinity of the optical axis and a convex-surface shape in a vicinity of the first reflection surface, the second face includes a second transmission surface formed with a center of the second transmission surface on the optical axis and a second reflection surface facing toward the front-object side and formed around the second transmission surface, the third face is configured as a transmission surface, and the following condition is satisfied:

$$1/f_{s\_21\_Mid} < 1/f_{s\_21\_Max}$$

where $f_{s\_21\_Mid}$ denotes a focal length of the reflective-refractive lens for a bundle of light rays having a chief ray that passes through the optical system as forming a middle angle of view in light from an approximately-lateral-object side, and $f_{s\_21\_Max}$ denotes a focal length of the reflective-refractive lens for a bundle of light rays having a chief ray that passes through the optical system as forming a maximum angle of view in the light from the approximately-lateral-object side.

5. An optical system for observing a front object and an approximately lateral object, wherein
- a first lens group with negative refractive power, a second lens group including a reflective-refractive lens, an aperture stop, and a third lens group with positive refractive power are arranged in that order from a front-object side,
- the reflective-refractive lens is provided with a first face arranged on the front-object side, a second face arranged on an image side, and a third face formed between the first face and the second face in a circumferential direction to surround an optical axis,
- the first face includes a first transmission surface formed with a center of the first transmission surface on the optical axis and a first reflection surface facing toward the image side and formed around the first transmission surface, and the first face is an aspherical surface that has a concave-surface shape in a vicinity of the optical axis and a convex-surface shape in a vicinity of the first reflection surface,
- the second face includes a second transmission surface formed with a center of the second transmission surface on the optical axis and a second reflection surface facing toward the front-object side and formed around the second transmission surface,
- the third face is configured as a transmission surface, and the following condition is satisfied:

$$f_{s\_21\_Mid} < 0$$

where $f_{s\_21\_Mid}$ denotes a focal length of the reflective-refractive lens for a bundle of light rays having a chief ray that passes through the optical system as forming a middle angle of view in light from an approximately-lateral-object side.

6. An optical system for observing a front object and an approximately lateral object, wherein
- a first lens group with negative refractive power, a second lens group including a reflective-refractive lens, an aperture stop, and a third lens group with positive refractive power are arranged in that order from a front-object side,
- the reflective-refractive lens is provided with a first face arranged on the front-object side, a second face arranged on an image side, and a third face formed between the first face and the second face in a circumferential direction to surround an optical axis,
- the first face includes a first transmission surface formed with a center of the first transmission surface on the optical axis and a first reflection surface facing toward the image side and formed around the first transmission surface, and the first face is an aspherical surface that has a concave-surface shape in a vicinity of the optical axis and a convex-surface shape in a vicinity of the first reflection surface,
- the second face includes a second transmission surface formed with a center of the second transmission surface on the optical axis and a second reflection surface facing toward the front-object side and formed around the second transmission surface,
- the third face is configured as a transmission surface, and the following condition is satisfied:

$$f_{s\_Mid} < f_{s\_Max}$$

where $f_{s\_Mid}$ denotes a focal length of the optical system for a bundle of light rays having a chief ray that passes through the optical system as forming a middle angle of view in light from an approximately-lateral-object side, and $f_{s\_Max}$ denotes a focal length of the optical system for a bundle of light rays having a chief ray that passes through the optical system as forming a maximum angle of view in the light from the approximately-lateral-object side.

* * * * *